United States Patent
Anderson et al.

(10) Patent No.: US 11,405,371 B2
(45) Date of Patent: Aug. 2, 2022

(54) METHODS AND SYSTEMS FOR BIOLOGICAL SEQUENCE COMPRESSION TRANSFER AND ENCRYPTION

(71) Applicant: Arc Bio, LLC, Cambridge, MA (US)

(72) Inventors: Jason Michael Anderson, Arlington, VA (US); David A Sinclair, Chestnut Hill, MA (US); Alejandro Quiroz-Zarate, Cambridge, MA (US); Roberto Olivares-Amaya, Somerville, MA (US); Ricardo Godinez-Moreno, Cambridge, MA (US)

(73) Assignee: ARC BIO, LLC, Cambridge, MA (US)

( * ) Notice: Subject to any disclaimer, the term of this patent is extended or adjusted under 35 U.S.C. 154(b) by 32 days.

(21) Appl. No.: 16/752,197

(22) Filed: Jan. 24, 2020

(65) Prior Publication Data
US 2020/0228507 A1 Jul. 16, 2020

Related U.S. Application Data

(62) Division of application No. 15/116,679, filed as application No. PCT/US2015/014651 on Feb. 5, 2015, now Pat. No. 10,630,812.
(Continued)

(51) Int. Cl.
*H04L 9/40* (2022.01)
*G16B 99/00* (2019.01)
(Continued)

(52) U.S. Cl.
CPC .......... *H04L 63/0471* (2013.01); *G16B 50/40* (2019.02); *G16B 50/50* (2019.02);
(Continued)

(58) Field of Classification Search
CPC ... H04L 63/0471; H04L 69/04; H04L 9/0618; H04L 9/0861; H04L 9/14; G16B 50/40; G16B 50/50; G16B 99/00; G16C 99/00
See application file for complete search history.

(56) References Cited

U.S. PATENT DOCUMENTS

| | | | |
|---|---|---|---|
| 5,537,551 A | 7/1996 | Denenberg et al. | |
| 10,673,826 B2 * | 6/2020 | Sinclair | H04L 9/12 |

(Continued)

FOREIGN PATENT DOCUMENTS

WO    2014151088 A2    9/2014

OTHER PUBLICATIONS

Cherniavksy, N. and Ladner, R. "Grammar-based compression of DNA sequences" in DIMACS Working Group on The Burrows-Wheeler Transform, 21 pages. 2004.
(Continued)

*Primary Examiner* — Thaddeus J Plecha
(74) *Attorney, Agent, or Firm* — Quarles & Brady LLP

(57) ABSTRACT

A device for compressing subject data. the device comprises a communication link, the communication link capable of receiving a set of subject data; a compression module, the compression module configured to apply a compression algorithm to the set of subject data, the compression algorithm compressing the set of subject data using a reference string of subject data; and a transmission module, the transmission module configured to transmit the compressed subject data. The device further comprising an encryption module for encrypting the subject data.

7 Claims, 16 Drawing Sheets

Specification includes a Sequence Listing.

Related U.S. Application Data

(60) Provisional application No. 61/936,147, filed on Feb. 5, 2014.

(51) Int. Cl.
  *G16B 50/50* (2019.01)
  *H04L 69/04* (2022.01)
  *G16C 99/00* (2019.01)
  *G16B 50/40* (2019.01)
  *H04L 9/06* (2006.01)
  *H04L 9/08* (2006.01)
  *H04L 9/14* (2006.01)

(52) U.S. Cl.
  CPC ............. *G16B 99/00* (2019.02); *G16C 99/00* (2019.02); *H04L 9/0618* (2013.01); *H04L 9/0861* (2013.01); *H04L 9/14* (2013.01); *H04L 69/04* (2013.01)

(56) References Cited

U.S. PATENT DOCUMENTS

| | | |
|---|---|---|
| 2003/0016821 A1 | 1/2003 | Hammersmith |
| 2003/0033168 A1 | 2/2003 | Califano et al. |
| 2004/0179682 A1* | 9/2004 | Soliman ................ H04L 9/0822 380/44 |
| 2005/0025232 A1 | 2/2005 | Parida et al. |
| 2008/0077607 A1 | 3/2008 | Gatawood et al. |
| 2008/0125978 A1 | 5/2008 | Robson et al. |
| 2011/0129086 A1* | 6/2011 | Schneider ............... H04L 9/065 380/42 |
| 2012/0236861 A1 | 9/2012 | Ganeshalingam et al. |
| 2013/0124292 A1* | 5/2013 | Juthani ................. H04B 63/083 705/14.26 |
| 2013/0185267 A1 | 7/2013 | Gatewood et al. |
| 2013/0238584 A1 | 9/2013 | Hendry |
| 2013/0246460 A1 | 9/2013 | Maltbie et al. |
| 2013/0282677 A1 | 10/2013 | Ji et al. |
| 2013/0304391 A1 | 11/2013 | Cardonha et al. |
| 2014/0038836 A1 | 2/2014 | Higgins et al. |
| 2014/0105382 A1* | 4/2014 | Liu ....................... H04L 9/0662 380/28 |
| 2014/0214780 A1 | 7/2014 | Lange et al. |
| 2014/0280327 A1 | 9/2014 | Pham et al. |
| 2014/0289536 A1 | 9/2014 | MacCarthy et al. |
| 2014/0369498 A1* | 12/2014 | Hammersmith ...... H04L 9/0822 380/46 |
| 2015/0154406 A1* | 6/2015 | Naehrig ................. G06F 21/602 713/165 |
| 2016/0125141 A1 | 5/2016 | Raisaro et al. |
| 2017/0085382 A1 | 3/2017 | Kamakari et al. |
| 2019/0087601 A1* | 3/2019 | Molyneaux ............ G16B 50/50 |
| 2021/0083862 A1* | 3/2021 | Pointcheval .......... H04L 9/0838 |

OTHER PUBLICATIONS

International Search Report and Written Opinion from parent PCT/US15/14651, dated Jul. 14, 2015, 21 pages.

International Search Report and Written Opinion from PCT/US2016/17166, dated Jun. 2, 2016, 17 pages.

Kuruppu, S., et al. "Iterative dictionary construction for compression of large DNA data sets." IEEE/ACM transactions on Computational Biology and Bioinformatics 9.1 (2011): 137-149.

* cited by examiner

CTGTCTCTTATACACATCTAGATGTGTATAAGAGACAGGTTTTTTTTTTAAAAAAAAAA 782　　　784　　786

SEQUENCE LISTING

```
<160> NUMBER OF SEQ ID NOS: 49

<210> SEQ ID NO 1
<211> LENGTH: 12
<212> TYPE: DNA
<213> ORGANISM: Artificial Sequence
<220> FEATURE:
<223> OTHER INFORMATION: synthetic

<400> SEQUENCE: 1
tataagagac ag                                                         12

<210> SEQ ID NO 2
<211> LENGTH: 12
<212> TYPE: DNA
<213> ORGANISM: Artificial Sequence
<220> FEATURE:
<223> OTHER INFORMATION: synthetic

<400> SEQUENCE: 2
gtataagaga ca                                                         12
```

<210> SEQ ID NO 3
<211> LENGTH: 12
<212> TYPE: DNA
<213> ORGANISM: Artificial Sequence
<220> FEATURE:
<223> OTHER INFORMATION: synthetic

<400> SEQUENCE: 3
tgtataagag ac								12

<210> SEQ ID NO 4
<211> LENGTH: 12
<212> TYPE: DNA
<213> ORGANISM: Artificial Sequence
<220> FEATURE:
<223> OTHER INFORMATION: synthetic

<400> SEQUENCE: 4
gtgtataaga ga								12

<210> SEQ ID NO 5
<211> LENGTH: 12
<212> TYPE: DNA
<213> ORGANISM: Artificial Sequence
<220> FEATURE:
<223> OTHER INFORMATION: synthetic

<400> SEQUENCE: 5
tgtgtataag ag								12

<210> SEQ ID NO 6
<211> LENGTH: 12
<212> TYPE: DNA
<213> ORGANISM: Artificial Sequence
<220> FEATURE:
<223> OTHER INFORMATION: synthetic

<400> SEQUENCE: 6
atgtgtataa ga								12

<210> SEQ ID NO 7
<211> LENGTH: 12
<212> TYPE: DNA
<213> ORGANISM: Artificial Sequence
<220> FEATURE:
<223> OTHER INFORMATION: synthetic

<400> SEQUENCE: 7
gatgtgtata ag								12

<210> SEQ ID NO 8
<211> LENGTH: 12
<212> TYPE: DNA
<213> ORGANISM: Artificial Sequence
<220> FEATURE:
<223> OTHER INFORMATION: synthetic

<400> SEQUENCE: 8
agatgtgtat aa								12

<210> SEQ ID NO 9
<211> LENGTH: 12
<212> TYPE: DNA
<213> ORGANISM: Artificial Sequence
<220> FEATURE:
<223> OTHER INFORMATION: synthetic

```
<400> SEQUENCE: 9
ttatacacat ct                                                        12

<210> SEQ ID NO 10
<211> LENGTH: 12
<212> TYPE: DNA
<213> ORGANISM: Artificial Sequence
<220> FEATURE:
<223> OTHER INFORMATION: synthetic

<400> SEQUENCE: 10
cttatacaca tc                                                        12

<210> SEQ ID NO 11
<211> LENGTH: 12
<212> TYPE: DNA
<213> ORGANISM: Artificial Sequence
<220> FEATURE:
<223> OTHER INFORMATION: synthetic

<400> SEQUENCE: 11
tagaatagac ag                                                        12

<210> SEQ ID NO 12
<211> LENGTH: 12
<212> TYPE: DNA
<213> ORGANISM: Artificial Sequence
<220> FEATURE:
<223> OTHER INFORMATION: synthetic

<400> SEQUENCE: 12
aataagagac ag                                                        12

<210> SEQ ID NO 13
<211> LENGTH: 12
<212> TYPE: DNA
<213> ORGANISM: Artificial Sequence
<220> FEATURE:
<223> OTHER INFORMATION: synthetic

<400> SEQUENCE: 13
ctgtctctta ta                                                        12

<210> SEQ ID NO 14
<211> LENGTH: 12
<212> TYPE: DNA
<213> ORGANISM: Artificial Sequence
<220> FEATURE:
<223> OTHER INFORMATION: synthetic

<400> SEQUENCE: 14
tgtctcttat ac                                                        12

<210> SEQ ID NO 15
<211> LENGTH: 12
<212> TYPE: DNA
<213> ORGANISM: Artificial Sequence
<220> FEATURE:
<223> OTHER INFORMATION: synthetic

<400> SEQUENCE: 15
gtctcttata ca                                                        12

<210> SEQ ID NO 16
```

```
<211> LENGTH: 12
<212> TYPE: DNA
<213> ORGANISM: Artificial Sequence
<220> FEATURE:
<223> OTHER INFORMATION: synthetic

<400> SEQUENCE: 16
tctcttatac ac                                                         12

<210> SEQ ID NO 17
<211> LENGTH: 12
<212> TYPE: DNA
<213> ORGANISM: Artificial Sequence
<220> FEATURE:
<223> OTHER INFORMATION: synthetic

<400> SEQUENCE: 17
ctcttataca ca                                                         12

<210> SEQ ID NO 18
<211> LENGTH: 12
<212> TYPE: DNA
<213> ORGANISM: Artificial Sequence
<220> FEATURE:
<223> OTHER INFORMATION: synthetic

<400> SEQUENCE: 18
tcttatacac at                                                         12

<210> SEQ ID NO 19
<211> LENGTH: 12
<212> TYPE: DNA
<213> ORGANISM: Artificial Sequence
<220> FEATURE:
<223> OTHER INFORMATION: synthetic

<400> SEQUENCE: 19
cttatacaca tc                                                         12

<210> SEQ ID NO 20
<211> LENGTH: 12
<212> TYPE: DNA
<213> ORGANISM: Artificial Sequence
<220> FEATURE:
<223> OTHER INFORMATION: synthetic

<400> SEQUENCE: 20
ttatacacat ct                                                         12

<210> SEQ ID NO 21
<211> LENGTH: 12
<212> TYPE: DNA
<213> ORGANISM: Artificial Sequence
<220> FEATURE:
<223> OTHER INFORMATION: synthetic

<400> SEQUENCE: 21
tatacacatc ta                                                         12

<210> SEQ ID NO 22
<211> LENGTH: 12
<212> TYPE: DNA
<213> ORGANISM: Artificial Sequence
<220> FEATURE:
<223> OTHER INFORMATION: synthetic

<400> SEQUENCE: 22
```

```
atacacatct ag                                              12

<210> SEQ ID NO 23
<211> LENGTH: 12
<212> TYPE: DNA
<213> ORGANISM: Artificial Sequence
<220> FEATURE:
<223> OTHER INFORMATION: synthetic

<400> SEQUENCE: 23
tacacatcta ga                                              12

<210> SEQ ID NO 24
<211> LENGTH: 12
<212> TYPE: DNA
<213> ORGANISM: Artificial Sequence
<220> FEATURE:
<223> OTHER INFORMATION: synthetic

<400> SEQUENCE: 24
acacatctag at                                              12

<210> SEQ ID NO 25
<211> LENGTH: 12
<212> TYPE: DNA
<213> ORGANISM: Artificial Sequence
<220> FEATURE:
<223> OTHER INFORMATION: synthetic

<400> SEQUENCE: 25
cacatctaga tg                                              12

<210> SEQ ID NO 26
<211> LENGTH: 12
<212> TYPE: DNA
<213> ORGANISM: Artificial Sequence
<220> FEATURE:
<223> OTHER INFORMATION: synthetic

<400> SEQUENCE: 26
acatctagat gt                                              12

<210> SEQ ID NO 27
<211> LENGTH: 12
<212> TYPE: DNA
<213> ORGANISM: Artificial Sequence
<220> FEATURE:
<223> OTHER INFORMATION: synthetic

<400> SEQUENCE: 27
catctagatg tg                                              12

<210> SEQ ID NO 28
<211> LENGTH: 12
<212> TYPE: DNA
<213> ORGANISM: Artificial Sequence
<220> FEATURE:
<223> OTHER INFORMATION: synthetic

<400> SEQUENCE: 28
atctagatgt gt                                              12

<210> SEQ ID NO 29
<211> LENGTH: 12
<212> TYPE: DNA
```

<213> ORGANISM: Artificial Sequence
<220> FEATURE:
<223> OTHER INFORMATION: synthetic

<400> SEQUENCE: 29
tctagatgtg ta        12

<210> SEQ ID NO 30
<211> LENGTH: 12
<212> TYPE: DNA
<213> ORGANISM: Artificial Sequence
<220> FEATURE:
<223> OTHER INFORMATION: synthetic

<400> SEQUENCE: 30
ctagatgtgt at        12

<210> SEQ ID NO 31
<211> LENGTH: 12
<212> TYPE: DNA
<213> ORGANISM: Artificial Sequence
<220> FEATURE:
<223> OTHER INFORMATION: synthetic

<400> SEQUENCE: 31
tagatgtgta ta        12

<210> SEQ ID NO 32
<211> LENGTH: 12
<212> TYPE: DNA
<213> ORGANISM: Artificial Sequence
<220> FEATURE:
<223> OTHER INFORMATION: synthetic

<400> SEQUENCE: 32
agatgtgtat aa        12

<210> SEQ ID NO 33
<211> LENGTH: 12
<212> TYPE: DNA
<213> ORGANISM: Artificial Sequence
<220> FEATURE:
<223> OTHER INFORMATION: synthetic

<400> SEQUENCE: 33
gatgtgtata ag        12

<210> SEQ ID NO 34
<211> LENGTH: 12
<212> TYPE: DNA
<213> ORGANISM: Artificial Sequence
<220> FEATURE:
<223> OTHER INFORMATION: synthetic

<400> SEQUENCE: 34
atgtgtataa ga        12

<210> SEQ ID NO 35
<211> LENGTH: 12
<212> TYPE: DNA
<213> ORGANISM: Artificial Sequence
<220> FEATURE:
<223> OTHER INFORMATION: synthetic

<400> SEQUENCE: 35
tgtgtataag ag        12

<210> SEQ ID NO 36
<211> LENGTH: 12
<212> TYPE: DNA
<213> ORGANISM: Artificial Sequence
<220> FEATURE:
<223> OTHER INFORMATION: synthetic

<400> SEQUENCE: 36
gtgtataaga ga                                                         12

<210> SEQ ID NO 37
<211> LENGTH: 12
<212> TYPE: DNA
<213> ORGANISM: Artificial Sequence
<220> FEATURE:
<223> OTHER INFORMATION: synthetic

<400> SEQUENCE: 37
tgtataagag ac                                                         12

<210> SEQ ID NO 38
<211> LENGTH: 12
<212> TYPE: DNA
<213> ORGANISM: Artificial Sequence
<220> FEATURE:
<223> OTHER INFORMATION: synthetic

<400> SEQUENCE: 38
gaataagaga ca                                                         12

<210> SEQ ID NO 39
<211> LENGTH: 12
<212> TYPE: DNA
<213> ORGANISM: Artificial Sequence
<220> FEATURE:
<223> OTHER INFORMATION: synthetic

<400> SEQUENCE: 39
tataagagac ag                                                         12

<210> SEQ ID NO 40
<211> LENGTH: 12
<212> TYPE: DNA
<213> ORGANISM: Artificial Sequence
<220> FEATURE:
<223> OTHER INFORMATION: synthetic

<400> SEQUENCE: 40
ataagagaca gg                                                         12

<210> SEQ ID NO 41
<211> LENGTH: 39
<212> TYPE: DNA
<213> ORGANISM: Artificial Sequence
<220> FEATURE:
<223> OTHER INFORMATION: synthetic

<400> SEQUENCE: 41
ctgtctctta tacacatcta gatgtgtata agagacagg                            39

<210> SEQ ID NO 42
<211> LENGTH: 59
<212> TYPE: DNA
<213> ORGANISM: Artificial Sequence
<220> FEATURE:

<223> OTHER INFORMATION: synthetic

<400> SEQUENCE: 42
ctgtctctta tacacatcta gatgtgtata agagacaggt ttttttttta aaaaaaaaa                59

<210> SEQ ID NO 43
<211> LENGTH: 34
<212> TYPE: DNA
<213> ORGANISM: Artificial Sequence
<220> FEATURE:
<223> OTHER INFORMATION: synthetic

<400> SEQUENCE: 43
accctaaccc taaccctaac cctaacccta accc                34

<210> SEQ ID NO 44
<211> LENGTH: 34
<212> TYPE: DNA
<213> ORGANISM: Artificial Sequence
<220> FEATURE:
<223> OTHER INFORMATION: synthetic

<400> SEQUENCE: 44
gttagggtta gggttagggt tagggttagg gtta                34

<210> SEQ ID NO 45
<211> LENGTH: 34
<212> TYPE: DNA
<213> ORGANISM: Artificial Sequence
<220> FEATURE:
<223> OTHER INFORMATION: synthetic

<400> SEQUENCE: 45
gaaccggaac cggaaccgga accggaaccg gaac                34

<210> SEQ ID NO 46
<211> LENGTH: 34
<212> TYPE: DNA
<213> ORGANISM: Artificial Sequence
<220> FEATURE:
<223> OTHER INFORMATION: synthetic

<400> SEQUENCE: 46
gaaccggaac cggaaccgga accggaaccg gaac                34

<210> SEQ ID NO 47
<211> LENGTH: 34
<212> TYPE: DNA
<213> ORGANISM: Artificial Sequence
<220> FEATURE:
<223> OTHER INFORMATION: synthetic

<400> SEQUENCE: 47
gttagggtta gggttagggt tagggttagg gtta                34

<210> SEQ ID NO 48
<211> LENGTH: 34
<212> TYPE: DNA
<213> ORGANISM: Artificial Sequence
<220> FEATURE:
<223> OTHER INFORMATION: synthetic

<400> SEQUENCE: 48
accctaaccc taaccctaac cctaacccta accc                34

```
<210> SEQ ID NO 49
<211> LENGTH: 21
<212> TYPE: DNA
<213> ORGANISM: Artificial Sequence
<220> FEATURE:
<223> OTHER INFORMATION: synthetic

<400> SEQUENCE: 49
acccctctat acacgcgaga g                                             21
```

METHODS AND SYSTEMS FOR BIOLOGICAL SEQUENCE COMPRESSION TRANSFER AND ENCRYPTION

CROSS-REFERENCE TO RELATED APPLICATIONS

This application is a divisional of co-pending U.S. patent application Ser. No. 15/116,679, filed on Aug. 4, 2016, which is a U.S. National Stage of PCT Application No. PCT/US2015/014651 filed on Feb. 5, 2015, which claims the benefit of U.S. Provisional Patent Application Ser. No. 61/936,147 filed on Feb. 5, 2014. Each of the preceding applications is hereby incorporated by reference herein in its entirety.

STATEMENT REGARDING FEDERALLY SPONSORED RESEARCH

Not Applicable

REFERENCE TO A SEQUENCE LISTING SUBMITTED VIA EFS-WEB

The content of the ASCII text file of the sequence listing named "155949_00029_ST25.txt" which is 9.25 kb in size was created on Mar. 4, 2020 and electronically submitted via EFS-Web herewith the application is incorporated herein by reference in its entirety.

BACKGROUND OF THE INVENTION

Biological sequencing is the process of determining the precise order of nucleotides within a biomolecule. For example, biomolecules can include DNA, RNA, mRNA, protein sequences and other bipolymers. The rapid development of sequencing methods and instruments has significantly advanced biological and medical research, and led to an increase in medical discoveries. This rapid development has led to biological sequencing being a critical tool for researchers and diagnosticians alike, in the medical field (e.g. personalized medicine, fertility screening, lifestyle choices, and health/lifespan predictions) as well as in fields such as forensic science, virology and systems biology.

This rapid development of sequencing methods and instruments over the last three decades has also resulted in high throughput sequencing technologies that have significantly improved the speed and precision of the analyzed sequences. This has resulted in researchers being able to collect massive quantities of high-precision data in very short times. However, processing of this data requires significant computing power to be able to be done quickly and accurately. Thus, multiple computers are often utilized to analyze data using parallel or distributed processing to simultaneously analyze thousands, millions or even billions of nucleotide sequences. While parallel and/or distributed processing can result in fast, precise sequencing results, the huge amount of data that must be processed and transmitted between the parallel or distributed computers can lead to inefficiencies in both the transmission of the data and the processing thereof. Similar issues exist for proteomic data generated from mass spectrometers. These files can be on the order of hundreds of gigabytes per sample and terabytes per run. This can result in inefficiencies in both the transmission of the data and the processing thereof. As new technologies continue to be devised to read genetic, epigenetic and proteomic data, this problem will be further compounded.

Further, the parallel and/or distributed processing computers may not always be in close proximity to each other, or connected via a secure network. Some may be connected over an open network topology accessible over the World Wide Web. This open link between processing computers can result in data privacy issues. In some instances, the data being transmitted can be medically privileged as it may be an individual's DNA, RNA, epigenetic DNA methylated phenotype, or proteomic data or even a part of the medical record. This data could also be privileged as it can contain data about other bloodline relatives, from which identity, whereabouts, health, age, personality traits, and disease susceptibility can be determined. In other instances, the data may be a new or novel discovery that would need to be protected to maintain a trade secret or other business advantage and even because of national security concerns. Currently, the data transmitted over open networks between parallel and/or distributed processing computers can potentially be intercepted and decoded. Currently, the transmitted data may not be encrypted or enciphered to a level appropriate to adequately mitigate the risks posed by hackers, state or non-state cyber actors with interests in the acquisition of sensitive data on specific individual groups.

SUMMARY OF THE INVENTION

The present invention overcomes the aforementioned drawbacks by providing methods and systems to compress biological sequence data, transfer the data, and decompress the data. The data compression and transfer can be achieved using a secure encryption process.

Specifically, and in accordance with one aspect of the present invention, a device for compressing biological data is provided. The device comprises a communication link, the communication link capable of receiving a set of biological data. The device further comprises a compression module, the compression module configured to apply a compression algorithm to the set of biological data, the compression algorithm compressing the set of biological data using a reference string of biological data; and a transmission module, the transmission module configured to transmit the compressed biological data.

In accordance with another aspect of the present invention, a device for encrypting biological data is provided. The device comprises a communication link, the communication link capable of receiving a set of biological data, the set of biological data including a plurality of biological data reads, the plurality of biological data reads having at least one data point. The device further comprises an encryption module, the encryption module encrypting the plurality of biological data reads using a single cipher encryption method. And, the device further comprises a transmission module, the transmission module configured to transmit the encrypted biological data.

In accordance with yet another aspect of the present invention, a method of compressing biological data is provided. The method comprises accessing a dictionary, the dictionary including a plurality of reference data; dividing the plurality of reference data into a plurality of data segments; determining a frequency of occurrence for each of the plurality of data segments; selecting a set of the plurality of data segments based on the frequency of occurrence. The method further comprises consolidating the set of data segments; creating a string reference of biological data;

receiving a read data; constructing a compound read string based on the received read data; comparing the compound read string to the string reference of biological data; and storing a position of a first overlapping data point between the compound read string and the string reference of biological data, and a length of the compound read string in a memory as compressed data.

In accordance with another aspect of the present invention, a method of encrypting biological data is provided. The method comprises generating a plurality of random keys for each of a plurality of biological data reads; associating the plurality of random keys to each of the plurality of biological data reads; assigning numerical values to every data point, the numerical value based on the value of the data point; and performing a modulo adding process to add the numerical values of the random key to the numerical values of the associated biological data read to generate an encrypted biological data read.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 8 illustrates an exemplary consolidated reference sequence (SEQ ID NOs:13-41).

FIG. 9 illustrates an exemplary string reference (SEQ ID NO:42).

DETAILED DESCRIPTION OF THE INVENTION

As discussed, it is common when analyzing biological molecules such as DNA, RNA, etc. to use a device commonly known as a sequencer in order to extract biological molecule sequence information from a sample containing the biological molecules. Additionally, protein sequencing devices can determine the amino acid/residue sequences of the proteins using mass spectrometry. Further, other methods of analyzing biological molecules such as sample preparation techniques or software, can, for example, determine DNA modifications, histone positioning, and protein modifications including histone modification (e.g. acetylation, methylation, ubiquitylation, proponylation, etc.). A common type of sequencer is a DNA sequencer. While reference is made in this application to "DNA sequencers," it should be understood that the disclosed DNA sequencers could be any type of biological molecule sequencer, capable of sequencing biological molecules, such as DNA, RNA, modified genetic material, protein, etc.

DNA sequencers are specialized scientific analysis instruments that work to automate the process of sequencing DNA. Specifically, DNA sequencers are used to determine the order of the four nucleobases found in DNA: adenine (A), guanine (G), cytosine (C) and thymine (T). The DNA sequencer can report the results of its analysis in a string consisting of the letters A, G, C and T organized in base pairs, which illustrate the DNA sequence of the sampled biological sample. Additionally, other bases can exist in simple lifeforms and in certain mammals at lower frequencies than A, C, G, T (e.g. uridine, 5-methyl-cytosine, 3-methylcytosine, 1-methylguanine, 7-methylguanine, N2-methylguanine, and N2-dimethylguanine, hydroxlated bases and covalently attached amino acids and multiply hexosylated side chains such as beta-D-glucosyl-hyroxymethyluracil). These elements can also be sequenced using sequencers. The final output of the sequencer can be organized and printed in a file that consists of a set of sequence strings of fixed length, which can contain a tremendous amount of data. For example, the human genome contains approximately 3 billion base pairs. These strings, after being sequenced, can then be analyzed in order to evaluate genomic entities, such as genes, transcription factors, etc. that are made up of groups of the base pairs. This analysis can be performed by a high-powered computer, or via multiple computers in parallel of distributed configurations. Parallel and/or distributed processing across multiple computers or computing devices can allow the analysis to be performed quickly, without the need for a high performance computer, such as a supercomputer or other similar parallel computing platform.

Figure 1:
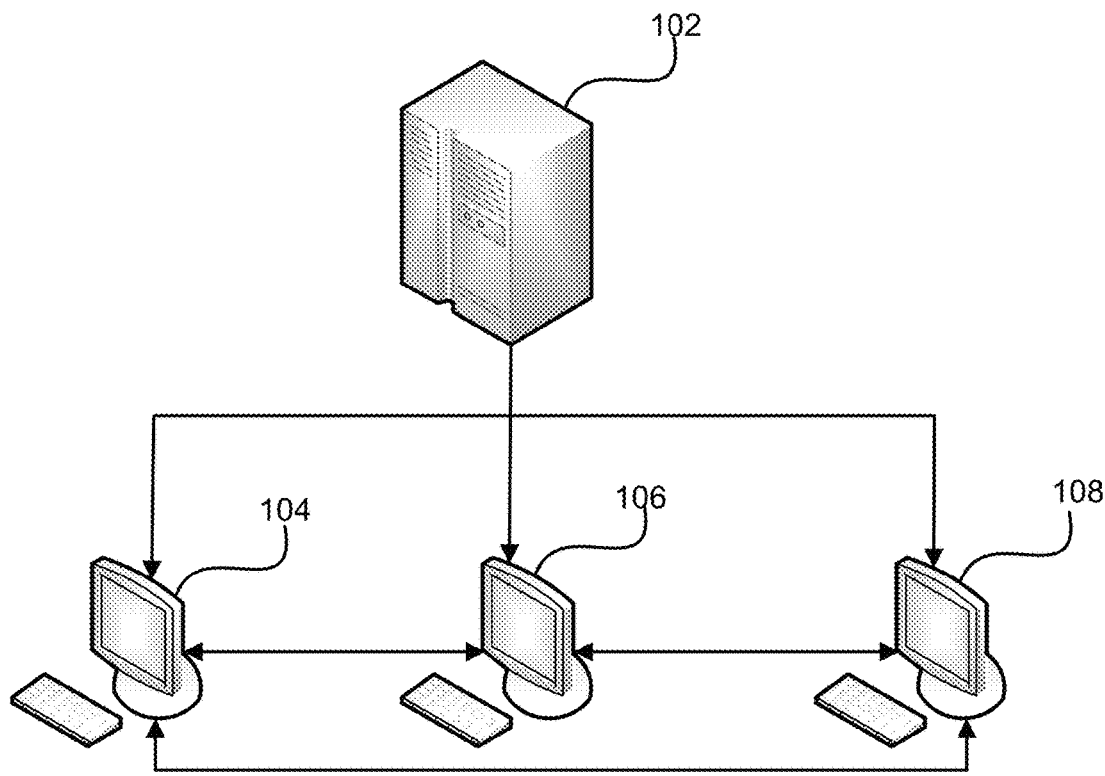
FIG. 1 is a system view of a parallel processing network.

FIG. 1 shows an illustrative example of a parallel processing network 100. Parallel processing network can have a sequencer platform 102. In one embodiment, the sequencer can be a DNA sequencer. However, the sequencer could be any type of biological molecule sequencer, such as an RNA sequencer platform. Non-limiting examples of types of sequencer platforms 102 can include single-molecule real-time sequencing, ion semiconductor, pyrosequencing, sequencing by synthesis, sequencing by ligation, and chain termination. As discussed above, the sequencer 102 can analyze a biological sample and sequence the nucleotides within the sample. Once the sequencer 102 has completely sequenced the biological sample, the resulting data can be transmitted to the parallel processing computers 104, 106, 108. In one example, the sequencer platform 102 can be itself be one of the parallel processing computers 104, 106, 108. Alternatively, the sequencer platform can be directly coupled to one of the parallel processing computers 104, 106, 108. It should be known that while three parallel processing computers 104, 106, 108 are shown, a parallel processing network could be comprised of more than three or less than three parallel processing computers. The parallel processing computers 104, 106, 108 can be any type of computer suitable for use. For example, the parallel processing computers can be Windows® based personal computers (PC) and portable devices, Apple® Macintosh® desktop and portable devices, Linux-based machines or any other type of computer that can run the necessary analysis. Additionally, the parallel processing computers could also include smartphones and/or other handheld devices and platforms. Further, it is not necessary that the individual parallel processing computers 104, 106, 108 be the same type of computer. Multiple types of computers can be used in the parallel processing network 100 simultaneously. In one example, the sequencer 102 can transmit the data directly to one of the parallel processing computers 104, 106, 108. Subsequently, the parallel processing computer 104, 106, 108 that receives the data can then determine if the work should be divided, and transmit the data to the other parallel processing computers 104, 106, 108. This process will be discussed in more detail below. Alternatively, the sequencer 102 can determine how to allocate the work between the parallel processing computers 104, 106, 108 and allocate the work to each individual parallel processing computer 104, 106, 108 as needed.

Figure 2:
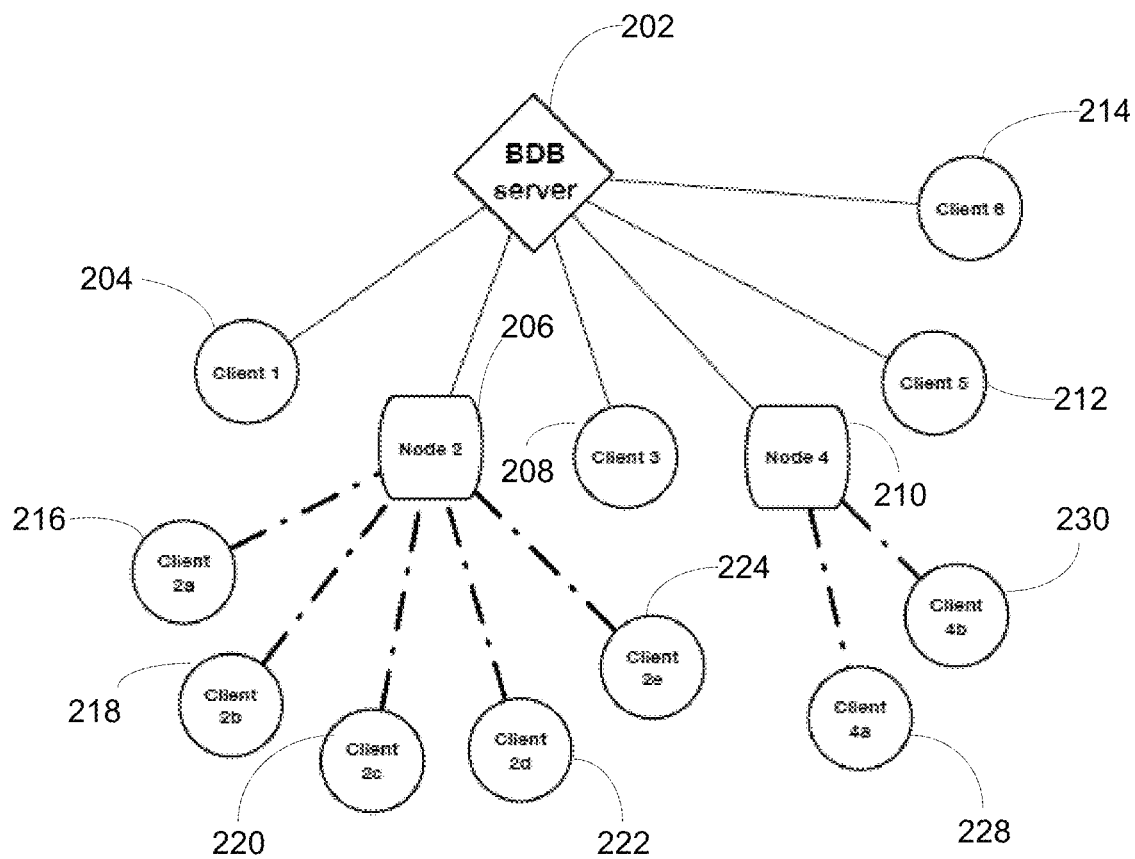
FIG. 2 is a system view illustrating a transfer of data from a sequencer between clients.

Turning now to FIG. 2, an example of a distributed network 200 can be seen. Distributed network 200 can include a main server 202. Main server 202 can be integrated into a sequencer device. Alternatively, the main server 202 can be a stand-alone computing device electrically coupled to one or more sequencer devices. The main server 202 can be in electrical communication with the sequencer device using multiple communication protocols. In one example, internet protocols such as User Datagram Protocol (UDP) or Transmission Control Protocol (TCP) can be used to provide SSL supported or similar type of encrypted communication between a sequencer device and the main server 202 over a data line. Alternative communication methods could be used as well; including, but not limited to: Universal Serial Bus (USB), firewire, fiber optic, high-speed earth to satellite to earth communication, Wi-Fi, Bluetooth, cellular (CDMA, GSA, 3G, 4G, LTE), radio frequency and any other type of communication technology between computing devices. Transfer of data could also be done via physical means, such as with hard drives and other high-capacity memory storage devices and large capacity memory access modules. In one embodiment, the main server 202 can be located offsite from the sequencing devices at a controlled server facility. For example, the main server could be located at a secure BigDataBio Center of Operations. Secure centrally operated servers, as well as other storage media can be configured to support encryption at rest, mitigating threat of compromise by both external and privileged access user (such as a system administrator). However, other secure servers and storage media can be used as the main server.

In one example, analysis devices 204, 206, 208, 210, 212, 214 can be connected to individual sequencing devices. The individual sequencing devices can generate sequencing information. The individual sequencing devices can subsequently transmit the generated sequencing information to the associated analysis device 204, 206, 208, 210, 212, 214 which can in turn transmit the sequencing data to central server 202. The central server 202 can then determine how to distribute the workload between the analysis devices 204, 206, 208, 210, 212, 214 in the distributed network. Thus, the main server 202 can act as the central brains of the distributed network, determining how best to distribute the work.

Main server 202 can then decide how to distribute the data between multiple other analysis devices 204, 206, 208, 210, 212, 214. The main server 202 can further assign and distribute the data received from the sequencing device to multiple other analysis devices 204, 206, 208, 210, 212, 214 for analysis. While the main server 202 is shown coupled to six analysis devices 204, 206, 208, 210, 212, 214 in FIG. 2, it should be known that the main server 202 can be coupled to more than six analysis devices or less than six analysis devices as required. Additionally, main server 202 can be used as to store the status of one or more sequencing devices. The main server 202 can store the status of the one or more analysis devices 204, 206, 208, 210, 212, 214. The main server 202 can communicate with the analysis devices 204, 206, 208, 210, 212, 214 using a UDP or TCP type communication, or other types of communication protocol as needed. For example, UDP, TCP/IP, USB, Firewire, fiber optic, satellite communication, cellular communication, radio frequency, etc. Some analysis devices 204, 208, 212, 214 can be single machine analysis devices. In one example single machine analysis devices 204, 208, 212, 214 can be dedicated biomolecule sequencing analysis devices. Alternatively, single machine analysis devices 204, 208, 212, 214 can be general purpose computing devices, such as PC's (Windows, Linux, UNIX, Mac), computer clusters, cloud computing devices, cellular phones (iOS, Windows, Android, etc.), tablets, gaming consoles, teslas, high-performance computer clusters, supercomputers, etc., which can be capable of analyzing and displaying the data provided by a sequencing device. Additionally, single machine analysis devices 204, 208, 212, 214 can be general purpose computing devices having a processor, a memory, and an operating system configured to perform executable instructions. Single machine analysis devices 204, 208, 212, 214 can further have display means for displaying data.

In one example, analysis devices 204, 206, 208, 210, 212, 214 can be connected to individual sequencing devices. The individual sequencing devices, having generated sequencing information, can transmit the data to the associated analysis device 204, 206, 208, 210, 212, 214 which can in turn transmit the sequencing data to central server 202, which can then determine how to distribute the workload between the analysis devices 204, 206, 208, 210, 212, 214 in the distributed network. Alternatively, central server 202 can instruct analysis devices 204, 206, 208, 210, 212, 214 to transmit data between each other as directed by central server 202. Thus, the main server 202 can act as the central brains of the distributed network, determining how best to distribute the work.

Additionally, some of the analysis devices can be multiple machine analysis devices 206, 210. For example, analysis device 206 can be in communication with multiple analysis sub-devices 216, 218, 220, 222, 224. In this situation, analysis device 206 can be a server simply directing the data received by the main server 202 to analysis sub-devices 216, 218, 220, 222, 224. Alternatively, analysis device 206 can itself be an analysis device that is further capable of distributing workload to multiple other analysis sub-devices 216, 218, 220, 222, 224. For example, analysis device 206 can be a dedicated biomolecule sequencing analysis device capable of distributing additional workload to other downstream analysis sub-devices 216, 218, 220, 222, 224; alternatively, analysis device 206 can be a general purpose computing device performing both analysis and facilitating communication to downstream analysis sub-devices 216, 218, 220, 222, 224. Furthermore, analysis sub-devices 216, 218, 220, 222, 224 can be dedicated biomolecule sequencing analysis devices; or, alternatively, general computing devices capable of analyzing the data provided by a sequencing device. Similarly, analysis device 210 can operate in the same manner as analysis device 206. For example, analysis device 210 can be in communication with multiple analysis sub-devices 228, 230. In this situation, analysis device 210 can be a server simply directing the data received by the main server 202 to analysis sub-devices 228, 230. Alternatively, analysis device 210 can itself be an analysis device that is further capable of distributing workload to multiple other analysis sub-devices 228, 230. For example, analysis device 210 can be a dedicated biomolecule sequencing analysis device capable of distributing additional workload to other downstream analysis sub-devices 228, 230; alternatively, analysis device 210 can be a general purpose computing device performing both analysis and facilitating communication to downstream analysis sub-devices 228, 230. Furthermore, analysis sub-devices 228, 230 can be dedicated biomolecule sequencing analysis devices; or, alternatively, general computing devices capable of analyzing the data provided by a sequencing device. The multiple machine analysis devices 206, 210 can communicate with their respective analysis sub-devices using standard internet protocols such as UDP or TCP. Alternatively, other communication methods such as TCP/IP, USB, Firewire, fiber optic, satellite communication, cellular communication, radio frequency, etc. could be used, as applicable.

It should be further known that any number of the analysis devices 204, 206, 208, 210, 212 can be single machine analysis devices or multiple machine analysis devices 206, 210 and that the arrangement shown in FIG. 2 is for example purposes. Accordingly it should be known that multiple configurations of single and multiple machine analysis devices is possible. Additionally, it should be known that a analysis sub-device may have additional sub-devices coupled to it for further distribution of the analysis. Additionally, the main server 202 may provide the data for analysis to certain of the analysis machines 204, 206, 208, 210, 212 depending on the type of data to be analyzed, or the type of analysis that is required. Thus, while in some instances data may be sent to every analysis machine 204, 206, 208, 210, 212, it may be the case in some applications that the data is sent to specific analysis machines as required.

As discussed, analyzing the data produced by a biomolecule sequencer currently requires massive computing power to efficiently obtain results. This can also be achieved with greater efficiency and speed by using a secure distributed network of analysis devices, such as those seen in FIG. 1 and FIG. 2. However, these systems can still be limited by the amount of data that must be transferred between the analysis devices. Thus methods and system for compressing the data to allow for ease of transmission is needed to provide additional efficiencies and speed to the analysis of sequenced biomolecule data. For clarity and consistency, the following descriptions of compression and deconvolution processes and devices shall refer to the processing of data from DNA sequencing. However, it should be noted that the following process and systems are applicable to other biomolecules, bioinformation, and subject or patient information, such as RNA, modified DNA, proteins, epigenetic data (e.g. DNA methylation patterns or histone acetylation patterns), peptide or protein sequences, DNA breakpoints, aneuploidy information (e.g. a loss or gain of a part of a chromosome), DNA copy number repeats (e.g. CNVs), genome deletion sites, medical data, historical records, phenotypic, genealogy, geolocation, etc. Additionally, while reference is made to the biomolecules, bioinformation, subject and/or patient information being related to the human subjects, the systems and methods described herein are also able to be used with bioinformation relating to animals, plants, pathogens, and synthetic or hybridized organisms.

Figure 3:
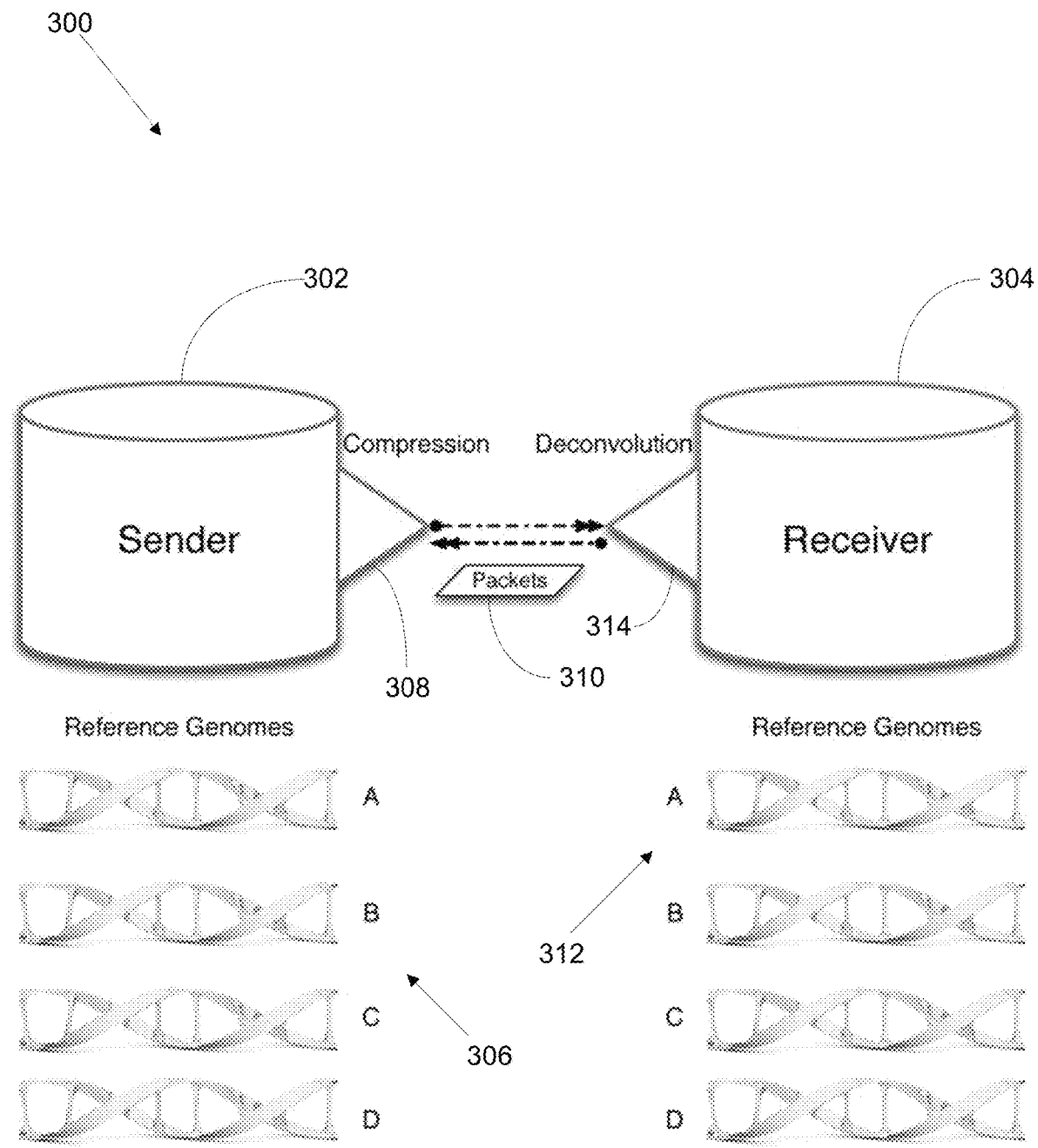
FIG. 3 is a system view illustrating data communication between two biomolecular data analysis devices.

FIG. 3 shows a communication interface 300 between a sender, or transmitting device 302 and a receiver 304. The sender 302 can be a device such as the main server 202 of FIG. 2. Alternatively, the sender 302 can also be an analysis device as discussed above. The sender could also be the sequencer platform 102 itself. In one embodiment, the sender module can contain a set of reference genomes in a genome library 306. The genome library 306 can contain commonly known genomes. Additionally, the genome library can contain partial genomes. While the genome library 306 of FIG. 3 shows only four individual genomes, it should be known that the genome library 306 can include more than four genomes or less than four genomes. The genome library 306 can be used by the compression module 308 of the sender in order to compress sequencing data as will be described in more detail below. The compression module 308 can compress the data into transmittable packets 310 which are then transmitted to the receiver 304. The receiver 304 can include a reference genome library 312 of its own. Receiver 304 genome library 312 can include the same reference genomes as genome library 306. The receiver 304 can then use the reference genomes in genome library 306 to decompress (deconvolute) the compressed data packets 310 using the deconvolution module 314 of the receiver 304.

Figure 4:
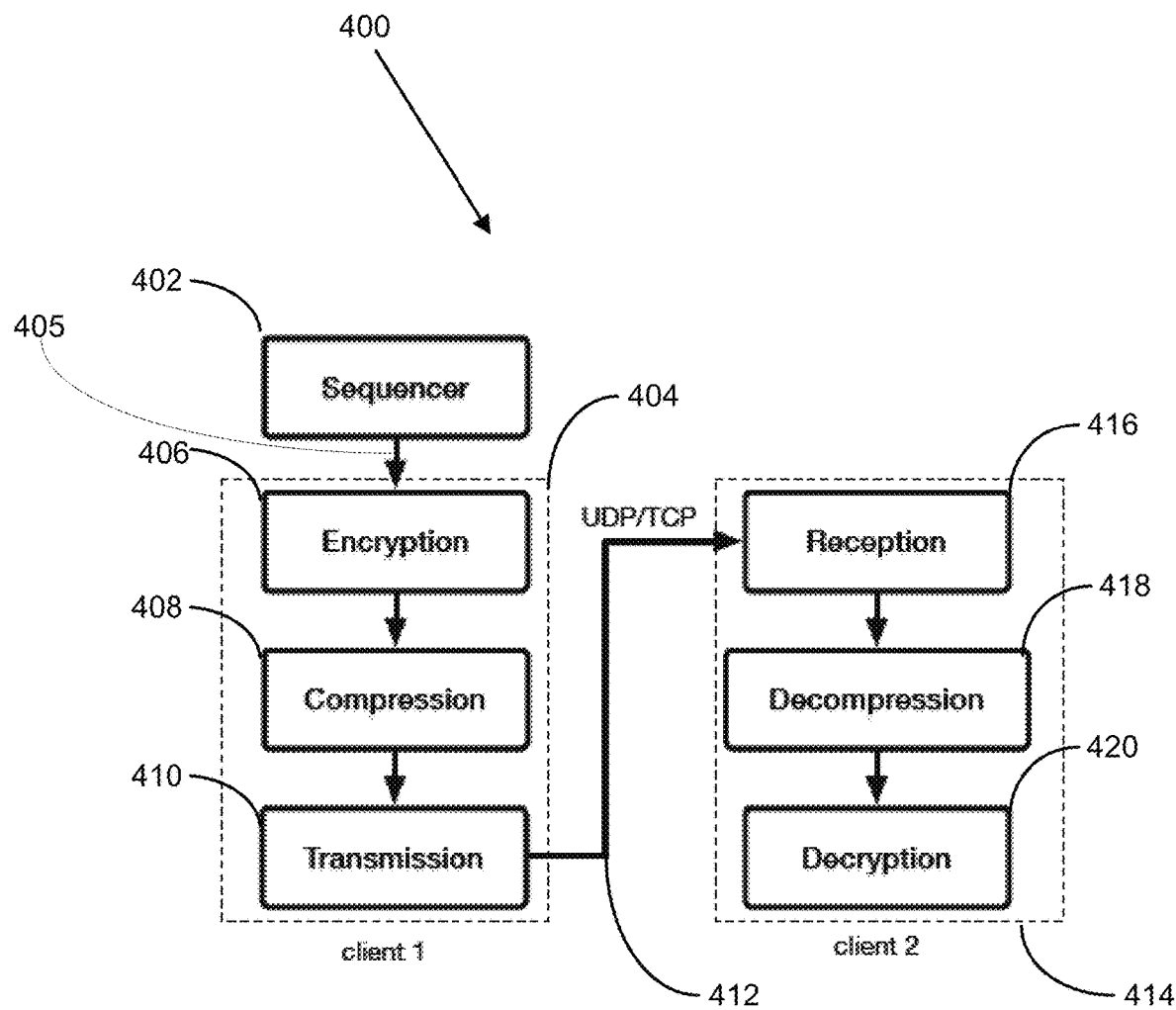
FIG. 4 is a system diagram illustrating a system for transmitting biomolecular data between analysis devices.

Turning now to FIG. 4, a system diagram showing a genome communication process 400 can be seen. A device, such as sequencer 402 can sequence a sample such as a biomolecule, e.g. DNA, and generate sequencing data. The sequencing data is then sent to analysis device 404. Analysis device 404 can be a stand-alone analysis device. As non-limiting examples, the analysis device 404 can be a dedicated sequence analysis machine, a PC or other computer, or a server. The analysis device 404 can receive the sequencing data over a communication link. In one embodiment, the communication link 405 can be a wired connection such as via a CAT5 cable, fiber optic, USB, etc. In other embodiments, the communication link 405 can also be a wireless connection such as Wi-Fi, Cellular (3G, 4G, LTE, etc.), Bluetooth, satellite communications, or any other communication technology between computing devices. Alternatively, analysis device 404 could be integral to a sequencing device. The analysis device can contain multiple modules, including an encryption module, a compression module and a transmission module, represented at 406, 408, 410 respectively. These modules can be implemented by software, hardware, or a hybrid of software and hardware. Non-limiting examples of hardware implementation could be performed using field-programmable gate arrays (FPGAs), graphical processing units (GPUs) and/or application-specific integrated circuits (ASICs).

When the data is received by the analysis device 404 it is encrypted at process block 406. Alternatively, the data can encrypted at the sequencer 402. The encryption can be done using multiple types of encryption technology. In one example, the encryption can be performed using a one time pad cipher for encryption, as discussed in more detail below. Additional, non-limiting examples of encryption methods can include cryptographically secure pseudorandom number generators, information-theoretically secure algorithms, integer factorization algorithms, primality tests, advanced access content system, symmetric-key algorithms, broken cryptography algorithms, cryptanalytic algorithms, and cryptographic hash functions. Furthermore, the encryption methods can utilize key pair concepts that utilize a public key, private key and/or passphrase (similar to that used in secure e-mail transfer). For example, the encrypting analysis device 404 would need to have the public key of the intended recipient device. Similarly, the intended recipient device would also have to have the public key of the encrypting analysis device 404. Alternatively, a keyed-hash message authentication code (HMAC) can also be used to generate a message authentication code using a cryptographic hash function in combination with a secret cryptographic key. This message authentication code can be used to verify both data integrity as well as to authenticate the sequence or data being transmitted. When encryption keys are used for sending and receiving sequence data, the keys can be generated randomly and can contain sufficient entropy. Entropy can be derived from unpredictable computer operations. For example, the movement of a disk drive head.

Additionally, alternative encryption methods can be employed. For example, a digital signature can be generated using the private key of a key pair. The digital signature can confirm that the biological sequence being sent was signed by the sender.

Once the sequencing data has been encrypted, the data can be compressed at process block 408. This compression can be performed by different compression methodologies, including read data compression and compression by reference. Both of these compression methodologies will be described in greater detail below.

Figure 5:
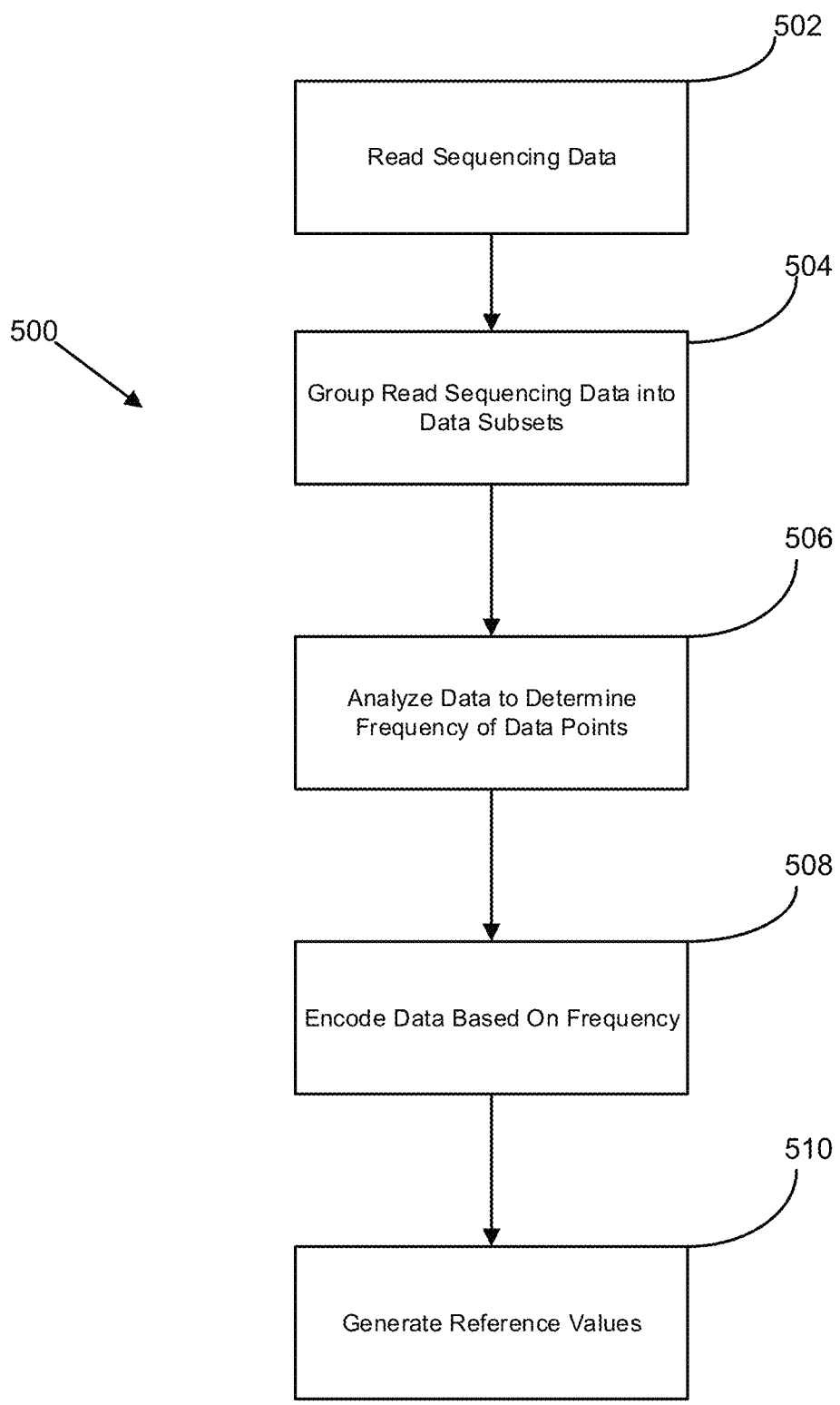
FIG. 5 is a flow chart illustrating a process for generating reference values.

In one embodiment, compression of the data provided by the sequencer can be accomplished using a compression method referred to as Read Data Compression. An exemplary Read Data Compression process 500 can be seen in FIG. 5. At process block 502, the sequencing data is read. In this example, it will be assumed that the sequencing data being read is in the form of DNA; however, other types of biomolecule sequences or bioinformation can also be used such as RNA, epigenetic data (e.g. DNA methylation patterns) and peptide or protein data. Phenotypic data could also be embedded within or appended to the biomolecule sequences. Furthermore, the Read Data Compression process 500 shown in FIG. 5, is outlined as being performed in a single iteration. While a single iteration is appropriate, it should also be known that Read Data Compression process 500 can be an multiple iteration process, thereby potentially allowing for more statistically significant data to be generated. Additionally, the sequencing data can be existing data, such as previous read data, known genome data, etc. In one embodiment, the sequencing data can be read by a module within the sequencer itself. Alternatively, the data can be transmitted to a separate analysis machine for reading. Once the sequencing data has been read, the sequencing data is then grouped into subsets of data points within the read sequencing data at process block 504. In one embodiment, the sequencing data can be broken up into groups of individual base elements (A, C, T, G) or other rarer bases (uridine, 5-methyl-cytosine, 3-methylcytosine, 1-methylguanine, 7-methylguanine, and N^2-methylguanine, and N^2-dimethylguanine) in groupings referred to herein as n-mers. These n-mers can be any length from 0 to the entire string of bases in the sequenced data. When determining what level of granularity the sequenced data should be broken down into when forming the n-mers, efficiency over using individual bases (A, C, T, G) can be evaluated. For example, using 12-mers (i.e. breaking the bases up into groups of 12 bases) can provide increased efficiency over evaluating individual bases, or 1-mers.

Once it is determined to what level the read data is to be divided into n-mers, it must be determined whether to evaluate the read data sequentially or per n-mer. For example, if it is determined to use 3-mers as the division of the read data, the 3-mers will contain different information depending on whether they are determined sequentially or per n-mer. For a given example set of read data of ACC-TACGAG, the resulting 3-mers, if done sequentially will produce seven 3-mers: ACC-CCT-CTA-TAC-ACG-CGA-GAG (SEQ ID NO:49). Alternatively, for the same set of read data, dividing the data per 3-mer results in: ACC-TAC-GAG. While both methods of assembling the n-mers are acceptable ways of defining n-mers, each has it own advantages. If the n-mers are determined sequentially, as described above, a more statistically relevant set of data can be produced. However, sequentially determining the n-mers also results in additional data points, thereby lowering the efficiency of the compression. In contrast, determining the n-mers per n-mer can reduce the number of data points, thereby increasing efficiency; but further resulting in a less statistically relevant process. For example, if there are 1,000,000 reads of length 101 bases (i.e. 101-mer), the complete read can be expressed as a complete set of 8-mers (i.e., there can be 4^8 possible 8-mers) when determining the n-mer sequentially. However, if using the per n-mer approach only 99.9% of the reads will be able to be expressed as 8-mers. This distinction is seen more clearly when 12-mers are used as the string length. In that instance, for 1,000,000 reads, approximately 34% of the potential elements can be determined using the sequential approach, while only 14% of the potential elements can be determined using the per n-mer approach.

Once the data has been grouped into n-mers, the read data n-mers are then analyzed to determine the frequency of occurrences of each of the given n-mers. Table 1 below shows an example of a frequency analysis of a series of 12-mers in a given read sample.

TABLE 1

| Symbol | Freq. |
| --- | --- |
| TATAAGAGACAG (SEQ ID NO: 1) | 148716356 |
| GTATAAGAGACA (SEQ ID NO: 2) | 147206629 |
| TGTATAAGAGAC (SEQ ID NO: 3) | 145728471 |
| GTGTATAAGAGA (SEQ ID NO: 4) | 144318777 |
| TGTGTATAAGAG (SEQ ID NO: 5) | 142938601 |
| ATGTGTATAAGA (SEQ ID NO: 6) | 141529357 |

TABLE 1-continued

| Symbol | Freq. |
|---|---|
| GATGTGTATAAG (SEQ ID NO: 7) | 139515907 |
| AGATGTGTATAA (SEQ ID NO: 8) | 136900535 |
| TTATACACATCT (SEQ ID NO: 9) | 126174239 |
| CTTATACACATC (SEQ ID NO: 10) | 125587499 |

The read data to be analyzed can be the entire set of read data. Alternatively, a percentage of the read data, a sub-set of the population, or even a variety of genomes within the overall read data can be analyzed to determine frequency of data points. Limiting the analysis to a sub-set of the data can be useful to accelerate the data analysis when it looking for a specific set of data within the overall read data.

Once the data has been analyzed to determine a frequency, the data can then be encoded at process block 508 based on the frequency of occurrence for a given n-mer as determined at process block 506. This encoding can allow a given n-mer to be expressed as a binary or base-2 value, thereby reducing the information needed to be transferred to represent the n-mer. In one embodiment, Huffman coding can be used to encode the read data. Huffman coding can allow for additional compression by also considering that some of the data sub-sets (n-mers) can be more prevalent than others. Thus, using Huffman coding, the more prevalent n-mers will be expressed using a smaller binary code, which can increase the efficiency of the compression. Additionally, when coding using Huffman encoding, minimum word sized (i.e., number of bits) can be determined. While Huffman encoding is illustrated in the example above, it should be known that other types of encoding could also be used to encode the sequencing data sorted by frequency. Additionally, the data to be encoded can be a sub-set of the total data that was gathered. For example, it may be determined that only the top n most frequent n-mers be encoded. Thus, based on the frequency of occurrence, a subset of the n-mers can represent a large section of the overall received sequencing data.

Additionally, n-mers can be evaluated that are similar to the top n most frequent n-mers, but do not occur so frequently to be included in a list of the top n most n-mers. For example, Table 1 shows a top occurring n-mer to be TATAAGAGACAG (SEQ ID NO:1). In a given read, a similar string may occur, for example TAGAATAGACAG (SEQ ID NO:11) and AATAAGAGACAG (SEQ ID NO:12) which vary from the top occurring n-mer by two bases and one base, respectively. In one embodiment, the above n-mers can be stored as reference values associated with a reference n-mer (e.g. TATAAGAGACAG (SEQ ID NO:1)), and then the offset and change of the similar strings can also be stored. For example, TAGAATAGACAG (SEQ ID NO:11) can be stored as 3G6T which can indicate that the third base of the reference n-mer should be changed to a G, and the sixth base should be changed to a T. This can allow for n-mers with similar base structures to top n-mers to be stored as based on offset position and value.

Once the sequence data has been encoded, the encoded n-mers can be stored as reference values at process block 510. The reference values can be used as a "key" for future data reads, and supplied to multiple analysis machines to allow for decoding of similarly encoded n-mers. The reference data can be stored in a memory of the analysis machines. Further, the reference data can be stored as a lookup table, an array, a searchable list, or other reference organization structure as is known in the art. The reference values can also be placed into a larger reference structure, which for purposes of this description can be referred to as a Dictionary. The Dictionary can contain reference values from the Read Data Compression process 500 as well as other data, such as commonly understood genomes. These reference values can be used to compress future sequencing data having similar structures, by expressing the specified n-mers as encoded values.

Figure 6:
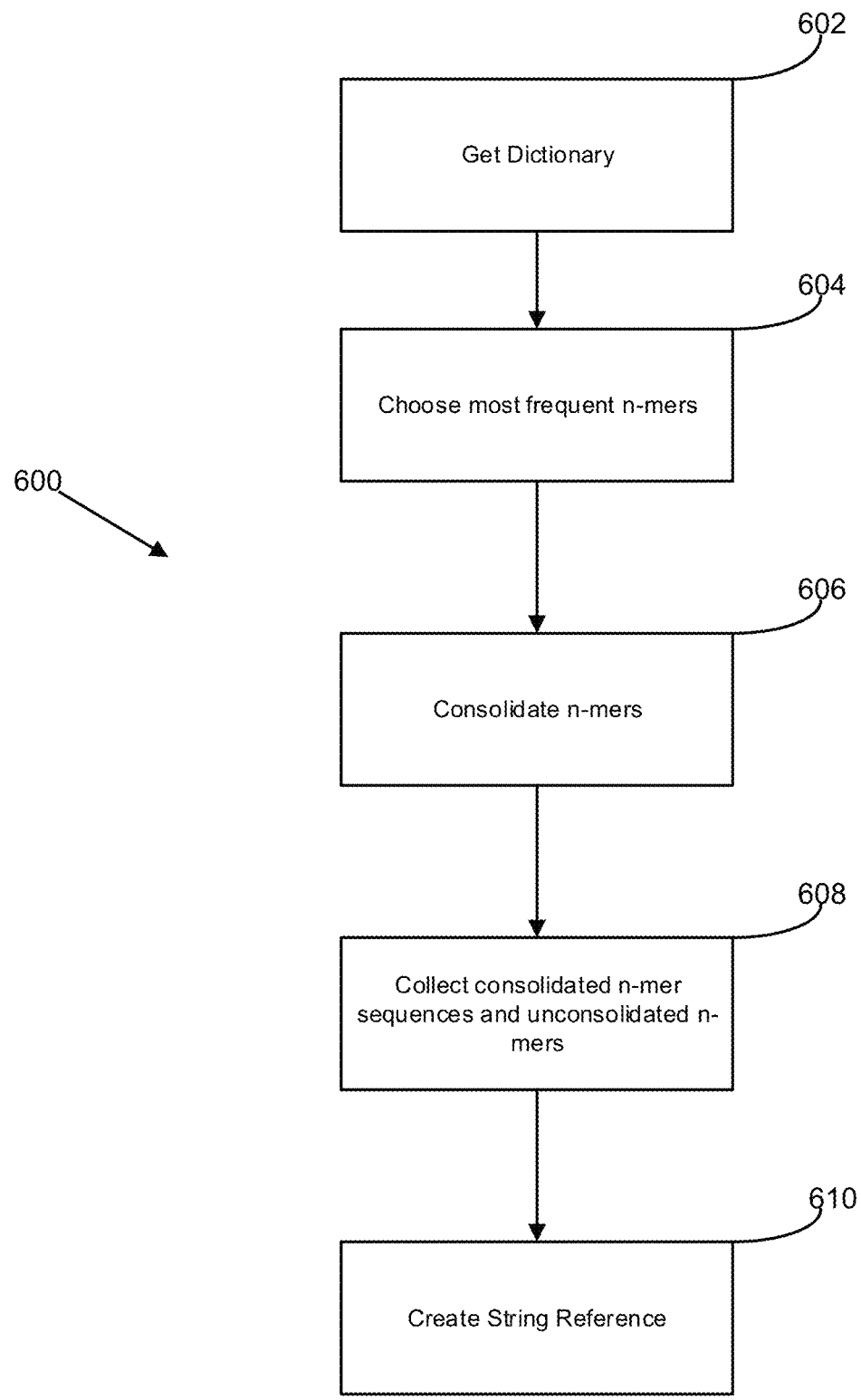
FIG. 6 is a flow chart illustrating a process for creating string references.

As discussed above, a compression by reference process can also be used. Prior to being able to compress data using the compression by reference, the reference data must be determined. Turning now to FIG. 6, an example of a reference determination process can be seen in the string formation process 600. In this example, a set of reference values, or a dictionary, is first accessed at process block 602. The dictionary can include data such as that gathered during a Read Data Compression process described above. Furthermore, the dictionary can contain commonly known genomes, as well as other relevant reference data. The dictionary can also include repetitive DNA sequences, which can represent 20-30% of the human genome. These repetitive DNA sequences can be implemented to create a library of repetitive elements which are prone to compression, due to their redundancy. This repetitive DNA can be compiled in a way that could also serve as a dictionary of molecular markers that would allow the identification and matching of any genome as a result of their respective informativity and/or hyper variability, which can allow for a fast and efficient identification of potentially any living organism as a species specific or even individual subject level. Examples of repetitive DNA elements can include Variable Number Tandem Repeats (VNTRs), Short Tandem Repetitive elements (STRs), Ribosomal RNA (rRNA), Transposons, Long Interspersed elements (LINES) and Short Interspersed elements (SINES). Additionally, the dictionary can contain RNA sequences, and variants. For example, small RNA sequences, metagenomic sequencing, and de novo Transcriptome sequencing. The dictionary can further include detailed identification of known regions with the data that can be difficult to sequence and/or can be determined only by sequencing data. Once the dictionary has been accessed, the most frequent n-mers in the Dictionary can be selected based on given parameters at process block 604. For example, the top 100 most frequent n-mers may be selected. However, more than 100 or less than 100 of the most frequent n-mers may also be selected, based on the type of analysis to be performed. In one embodiment, the quantity of most frequent n-mers selected can be determined by a user. Alternatively, an analysis device may automatically choose the number of most frequent n-mers selected based in order to optimize the compression.

Figure 7:
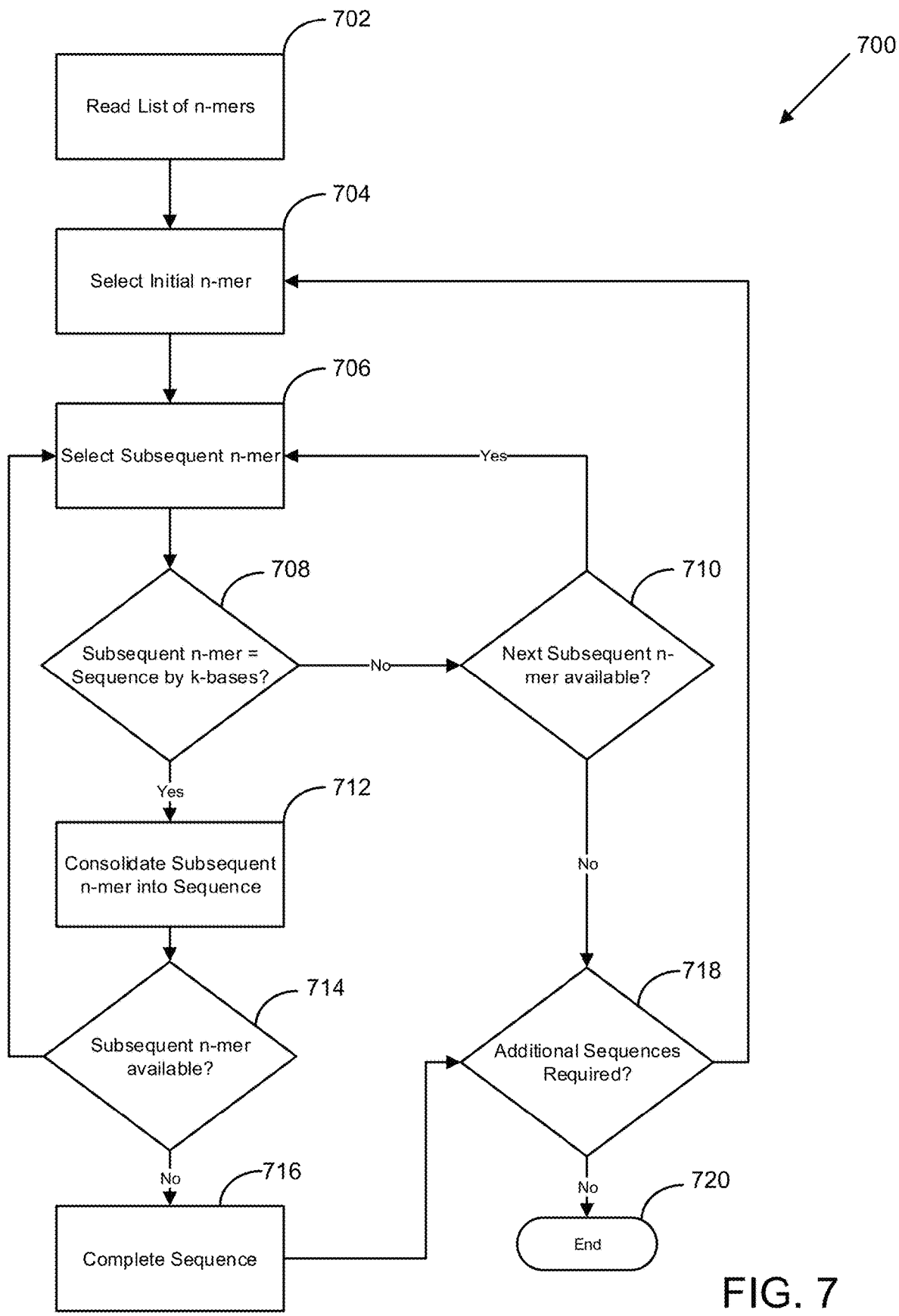
FIG. 7 is a flow chart describing a processing for generating consolidated genetic base sequences.

At process block 606, the selected most frequent n-mers can be consolidated. In one embodiment, the n-mers can be consolidated using a consolidation process 700 as shown in FIG. 7. At process block 702 a list of n-mers can be read. The list of n-mers can be a set of read data from a sequencer, which has been divided into n-mer sections; for example, 12-mers. Additionally, the list of n-mers can be a list of n-mers previously sorted by frequency, such as those values determined in the string formation process 600. Proceeding to process block 704 the read consolidation process 700 can select an initial n-mer from the overall list of n-mers. This first n-mer can be designated as a sequence; for example, a first sequence. The first n-mer selected can be the n-mer determined to have the highest frequency of occurrence in the read data. However, alternative methods can be used to select the first n-mer. For example, the first n-mer could be determined using known codon sequences, anticodon sequences, other RNA sequences, amino acid residue information, and genomic-based prevalence. The read consolidation process 700 can then proceed to process block 706 and select a subsequent n-mer from the list of n-mers. The read consolidation process 700 can select the subsequent n-mer based on selecting the next n-mer in the available series. Alternatively, the read consolidation process 700 can select the subsequent n-mer based on other criteria.

At process block 708 the read consolidation process 700 can compare the subsequent n-mer to the first sequence to determine if there is an overlap of base elements (A, T, C, G). Specifically, the comparison can be set to determine if the subsequent n-mer is equal to the first sequence up to a specified number (k) of bases. While the number of bases representing k can be any number, in order to facilitate ease and reliability into the comparison k can be equal to n−1, where n is equal to the number of bases in the n-mer. Using k=n−1 allows for a robust k value which can provide a higher certainty that a given n-mer in fact belongs to a much larger string. Relying on overlaps smaller than k=n−1 can lead to potentially larger strings, but a reduction in certainty that said read could exist. However, reducing the overlap beyond k=n−1 can allow for potentially larger strings to be concatenated. Values of k can also be established by determining a point in which there exists an impermissible quality level for each of the nucleotides that form a read (sometimes 50, sometimes between 100-150, 150-200, and sometimes even larger, for example 1 k-100 k. It should be known that values of k can be even greater than 100 k in some instances. If the subsequent n-mer is not equal to at least k-bases of the first sequence, the read consolidation process can then determine if a next subsequent n-mer is available in the list of n-mers at process block 710. If the next subsequent n-mer is available, the read consolidation process can return to process block 706 and select another subsequent n-mer from the list of n-mers. If the next subsequent n-mer is not available, the read consolidation process can proceed to process block 718, discussed in more detail below.

If the subsequent n-mer is equal to at least k-bases of the first sequence, the read consolidation process 700 can consolidate the subsequent n-mer into the first sequence at process block 712. After the subsequent n-mer is consolidated into the first sequence, the read consolidation process can determine if a subsequent n-mer is available to compare with the first sequence at process block 714. If there is a subsequent n-mer available, the process returns to process block 706. However, if another subsequent n-mer is not available, for example if all of the n-mers in the list of n-mers have been compared against the first sequence, the process can determine that the first sequence is completely consolidated at process block 716. The read consolidation process 700 determining that the first sequence is completed at process block 716 can store the completed first sequence in a memory. At process block 718 the read consolidation process 700 can determine if more sequences are required to be consolidated. For example, if there were a determined percentage of the n-mers in the list of n-mers were not able to be consolidated into the first sequence, it may be necessary to consolidate at least an additional sequence. In one example, consolidation can be performed recursively. First, the reads that are up to n−1 in similarity can be consolidated. After the n−1 reads have been consolidated, the n−2, n−3, etc reads can subsequently be consolidated. Alternatively, to optimize speed, a single consolidation only can be performed. Where there are multiple reads of like type (n−1, n−2, etc.), the consolidation process 700 can consolidate the reads based on a tie-breaking criteria. In one embodiment, the tie-breaking criteria can be the frequency of occurrence for a given n-mer. For example, for a sequence ACGGGG, two possible subsequent n-mers can be CGGGGA and CGGGGT. In this example both the subsequent n-mers are k=n−1 matches. Thus, in this instance, the subsequent with the highest frequency of occurrence will be consolidated with the sequence.

Figure 8:
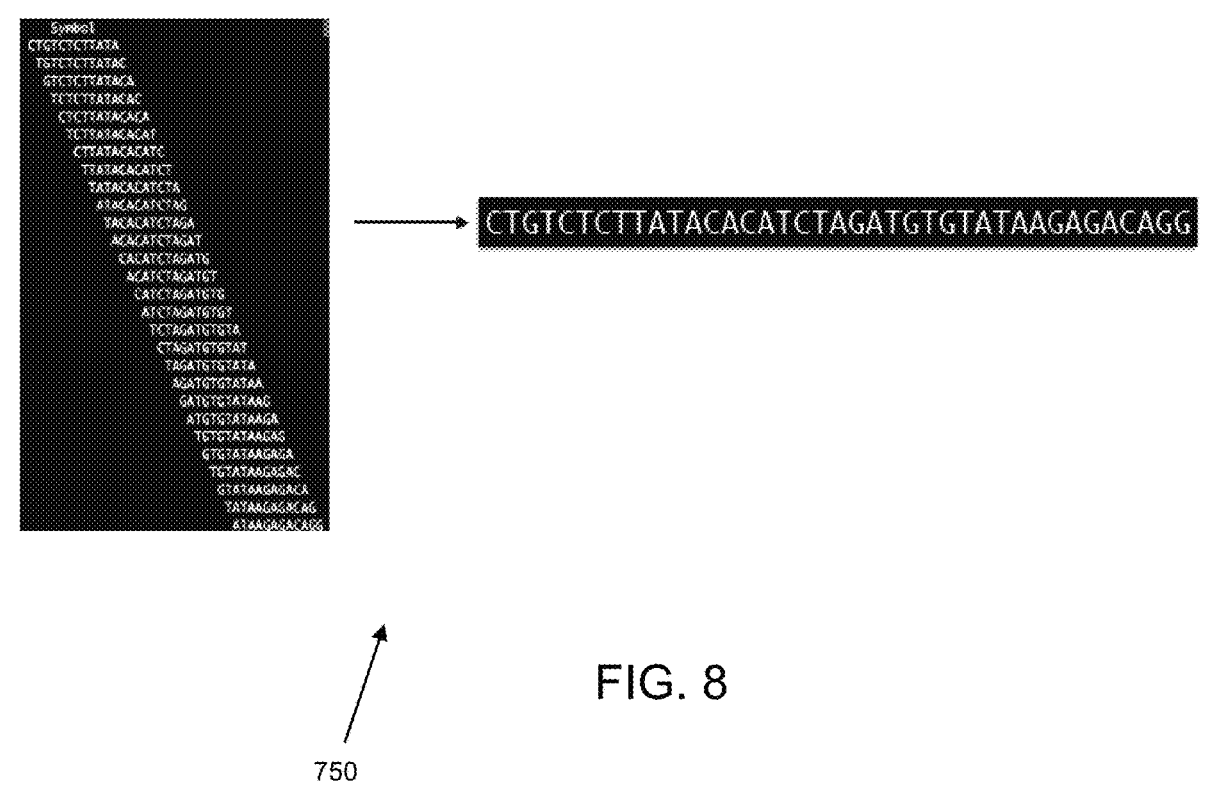

If, at process block 718 it is determined that additional sequences should be consolidated, the read consolidation process can return to process block 704. If the read consolidation process determines that no additional sequences are required to be consolidated, the read consolidation process can end at process block 720. Turning briefly to FIG. 8, an example of a consolidated sequence 750 can be seen.

Returning now to FIG. 6, once the n-mers have been consolidated, the string formation process 600 can proceed to process block 608 to collect both the consolidated n-mer sequences as well as the unconsolidated n-mers. Unconsolidated n-mers can be the n-mers which were unable to be consolidated into larger sequences at process block 606. Once the consolidated n-mer sequences and the unconsolidated n-mers are collected at process block 608, they can be combined into a single string reference at process block 610. Each of the consolidated n-mer sequences and the unconsolidated n-mers can be given a position reference to record the location of the n-mers within the string reference. The string can be formed with the consolidated n-mer sequences at a first end of the string, and the unconsolidated n-mers positioned at a second end of the string reference. However, unconsolidated n-mers can be located between consolidated sequences or even at the beginning of the string reference, provided that the location within the string reference is known.

FIG. 9 shows a exemplary string reference 780. String reference 780 has both a consolidated n-mer sequence 782 and unconsolidated n-mers 784 and 786. In this example, the unconsolidated n-mers are shown to be 12-mers; however, they could be any length of n-mer as required. Additionally, the consolidated n-mer sequences is shown to be 39 bases in length. However, the consolidated n-mer sequences can be any length as determined in the read consolidation process 700. Further, string reference 780 is shown to be 67 characters in length, however, string references can contain more than 67 characters. In one embodiment, the string reference length can be 32,000 characters.

Figure 10:
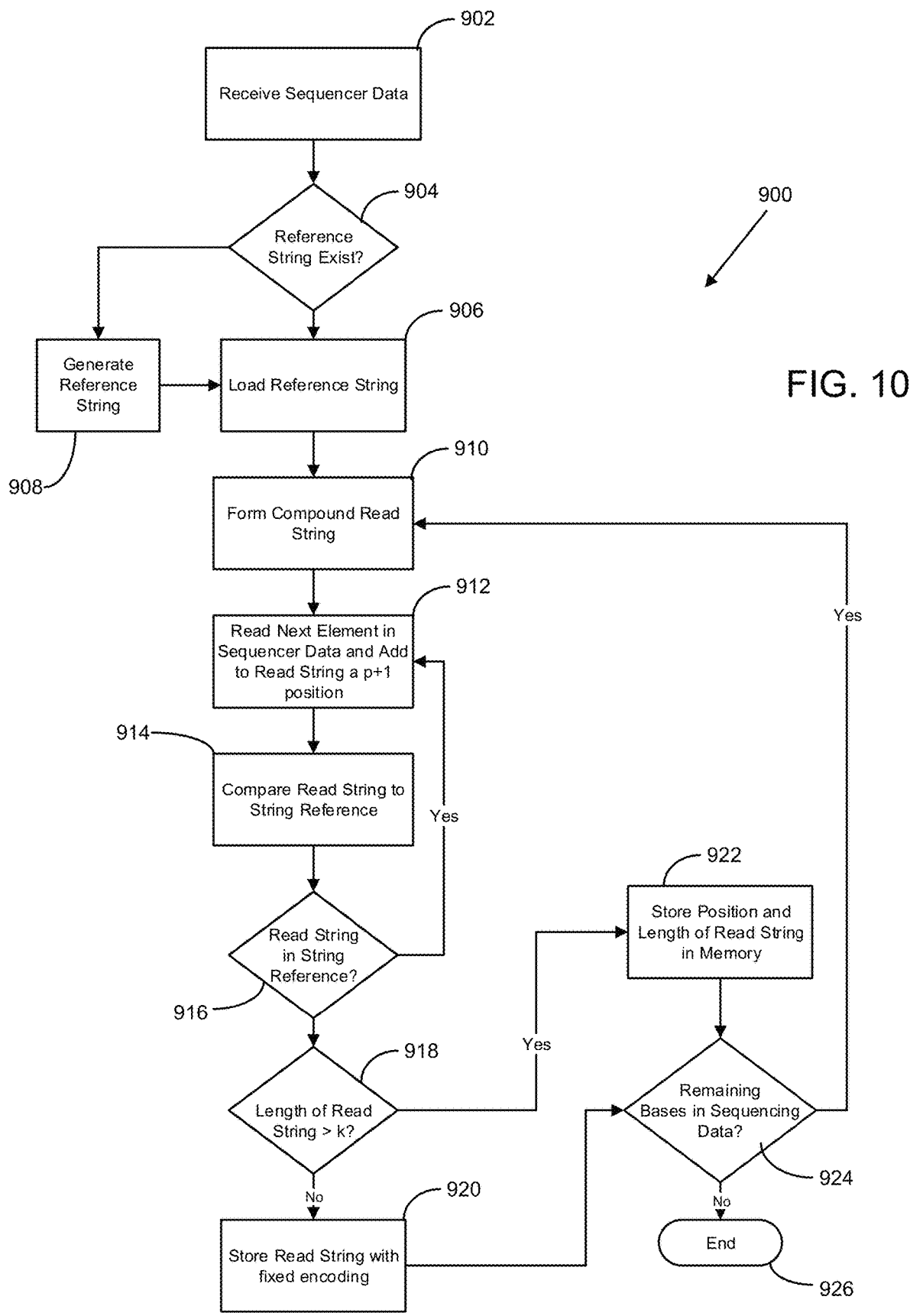
FIG. 10 is a flow chart illustrating a process for compressing sequencing data using compression by reference.

Turning now to FIG. 10, a reference compression process 900 can be seen. At process block 902 the reference compression process 900 receives sequence data, such as from a sequencer. Once the sequence data is received, the reference compression process determines if a reference string exists in memory at process block 904. If a reference string does exist, the process can load the reference string at process block 906. If a reference string does not exist, the reference compression process 900 can proceed to generate a reference string at process block 908. To generate a reference string, the reference compression process can initiate a string formation process, such as that shown in FIG. 6, and discussed above. Once the reference string is generated at process block 908, the reference string can be loaded at process block 906. Once the reference string has been loaded, the reference compression process 900 can proceed to form a compound read string at process block 910. A compound read string is a section of the sequencing data that is to be compared to the reference string. The reference string, in this example is initially set to contain a single base. In one embodiment, to form the compound read string, the first base in the sequencing data can be the initial compound read string. However, in other embodiments, the compound read string can use a different base in the sequencing data as the starting point. In one embodiment, the compound read string can be initialized to have zero data points. The compound read string can then be started (i.e. establish the first data point) based on the first letter received from the read data. Alternatively, other methods of determining the initial compound read string can be based on reading the read data as reverse complement.

Once the first compound read string has been formed at process block 910, the reference compression process 900 can read the next sequential base element in the sequencer data and add the sequential element to the compound read string to increase the length of the compound read string by a single base at process block 912. In order to maintain consistency and accurate data compression, the next sequential base element can be added to the compound read string in a position corresponding to the position of the sequential base in the original sequencing data.

The compound read string can be then compared to the string reference to determine if the compound read string corresponds to a portion of the reference string at process block 914. If the compound read string is found to correspond to a portion of the reference string at process block 916, the process returns to process block 912 to read and add the next base element of the sequencer data to the compound read string. If the compound read string is not found to correspond to a portion of the reference string, the reference compression process 900 then evaluates the length of the compound read string against a preset length value at process block 918. The preset length value can be determined to be a length that is sufficient to prevent small groupings of bases from being compressed using the reference string, thereby increasing processing time. For example, the preset length value may require the compound read string to be greater than a 3-mer. However, it should be known that more than 3 base elements or less 3 base elements can be used for the predetermined length value.

If the length of the compound read string is less than the predetermined length value, the compound read string can be stored using a fixed encoding method at process block 920. An example of fixed encoding could be to convert the compound read string to a base-4 value (A, C, G, T). Alternatively, other encoding values such as Hex, ASCII, Huffman codes, etc., could be used to encode the compound read string using fixed encoding methods. Alternatively, if the length of the compound read string is determined to be greater than the predetermined length value, the reference compression process 900 can then store the position and length of the overlapping portion of the reference string and the compound string reference in memory. For example, if the length of the compound read string is 101 characters, and corresponds to a portion of the reference string starting at the 756th bases element in the reference string, the compound read string can be stored as position 756; length 101. Alternatively, other methods of storing the position and length of the compound read string in memory can additionally be used, such as storing only the starting position and ending position. For example, using the data above, the compound read string could be stored as 756:857. Additionally, the position and length of the compound read string could be stored with a distance with respect to 0 (i.e. with negative signs in case the data type is not unsigned). The position and length of the compound read string can also be stored by storing all compound strings of equal length in 1 column or row in a data table. Subsequently, only the offset of the compound string in the reference string and not the length or end offset would be required to be stored. Further, to aid in reducing memory requirements by reducing the use of large integers to represent the offsets (i.e. where reference string is long value, such as 32,000 characters), sequential offsets can be stored in relation to the previous offset. Offset values could also be reduced by factoring out prime or multiplicative numbers as well.

Once the compound read string has been stored in memory at either process block 920 or 922 the reference compression process 900 can then determine if there are remaining bases that have not yet been encoded and stored, contained within the sequencing data at process block 924. If there are remaining bases, the reference compression process 900 can return to process block 910 to continue processing the remaining blocks, by forming subsequent compound read strings. Alternatively, if it is determined at process block 924 that there are no remaining bases to be encoded and stored in the sequencing data, the reference compression process can end at process block 926.

Returning to FIG. 4, once the sequencing data has been compressed, it is prepared for transmission to analysis machine 414 at transmission module 410. The compressed data can be transmitted using a variety of protocols. In one example, the compressed data can be packaged for transmission over an internet based protocol such as UDP, TCP, TCP/IP, SCTP, RSVP, DDCP or other known transport layers. Alternatively, the compressed data can be packaged for other transmission protocols such as burst transmissions, or satellite communication. Once the compressed data has been prepared for transmission, the compressed data can be transmitted to analysis machine 414 over communication link 412. In one embodiment, the communication link 412 can be a wired link such as an Ethernet cable, i.e. CAT5 cable. The communication link 412 could also be other wired connections such as serial, USB, Firewire, or fiber optic. Alternatively, the communication link 412 can be a wireless link such as Wi-Fi, near field communication, microwave, radio, or Bluetooth®, etc.

Analysis machine 414 can receive the compressed data via the communication link 412 at reception module 416. Reception module 416 can be configured to receive information transmitted by transmission module 410 using a particular protocol, as described above. Once the data has been received, it is then decompressed at decompression block 418 before it is then decrypted at decryption module 420.

Figure 11:
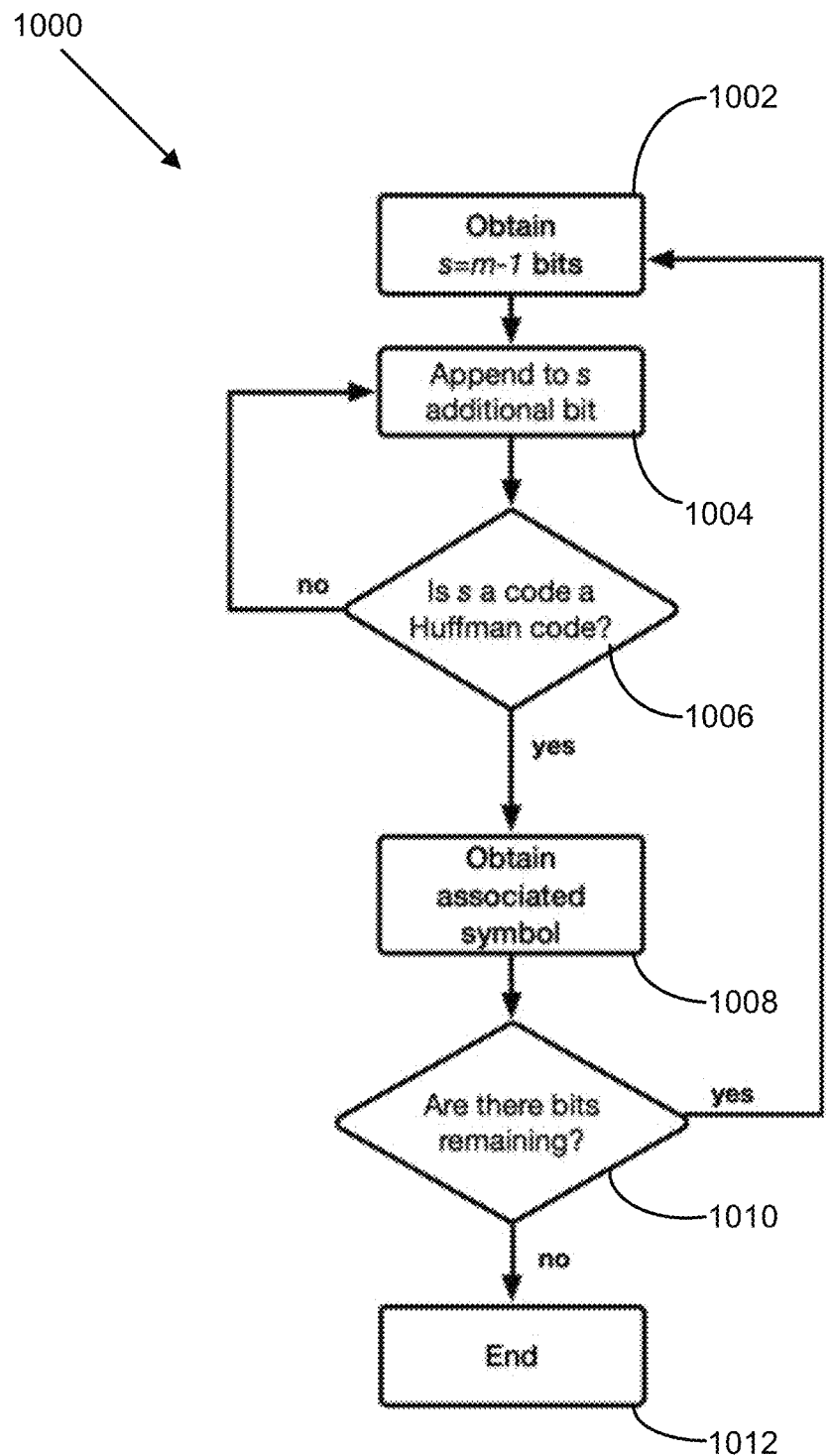
FIG. 11 is a flow chart illustrating a process for decompressing Huffman coded sequencing data.

Turning to FIG. 11, an example Huffman decompression process 1000 can be seen. At process block 1002 the Huffman decompression process 1000 receives compressed data in the form of s=m−1 bits. As the minimum length of a Huffman compressed code is m, the data is first processed as m−1 bits. Proceeding to process block 1004, an additional bit is then added to the data segment s. Once the bit has been added to data segment s at process block 1004, the data segment s can then evaluated to see if it corresponds to a predetermined Huffman code stored in memory at process block 1006. If the data segment s does not correspond to a predetermined Huffman code, the Huffman decompression process 1000 can return to process block 1004 to add an additional bit to the data segment s. If the data segment s is determined to correspond to a Huffman code, the sequencing data segment (i.e. n-mer) associated with the Huffman code can be determined at process block 1008. In one embodiment, the Huffman code can be equated with its corresponding sequencing data segment by evaluating a stored reference database, such as a look up table, containing the Huffman codes and their corresponding sequencing data segment.

Once the sequencing data segment associated with the Huffman code has been determined, the Huffman decompression process 1000 can determine if there are any additional bits remaining in the received sequencing data at process block 1010. If there are bits remaining in the received sequencing data, the Huffman decompression process 1000 can then return process block 1002 to process the remaining bits. If it is determined that there are no additional bits remaining at process block 1010, the Huffman decompression process can end at process block 1012.

Figure 12:
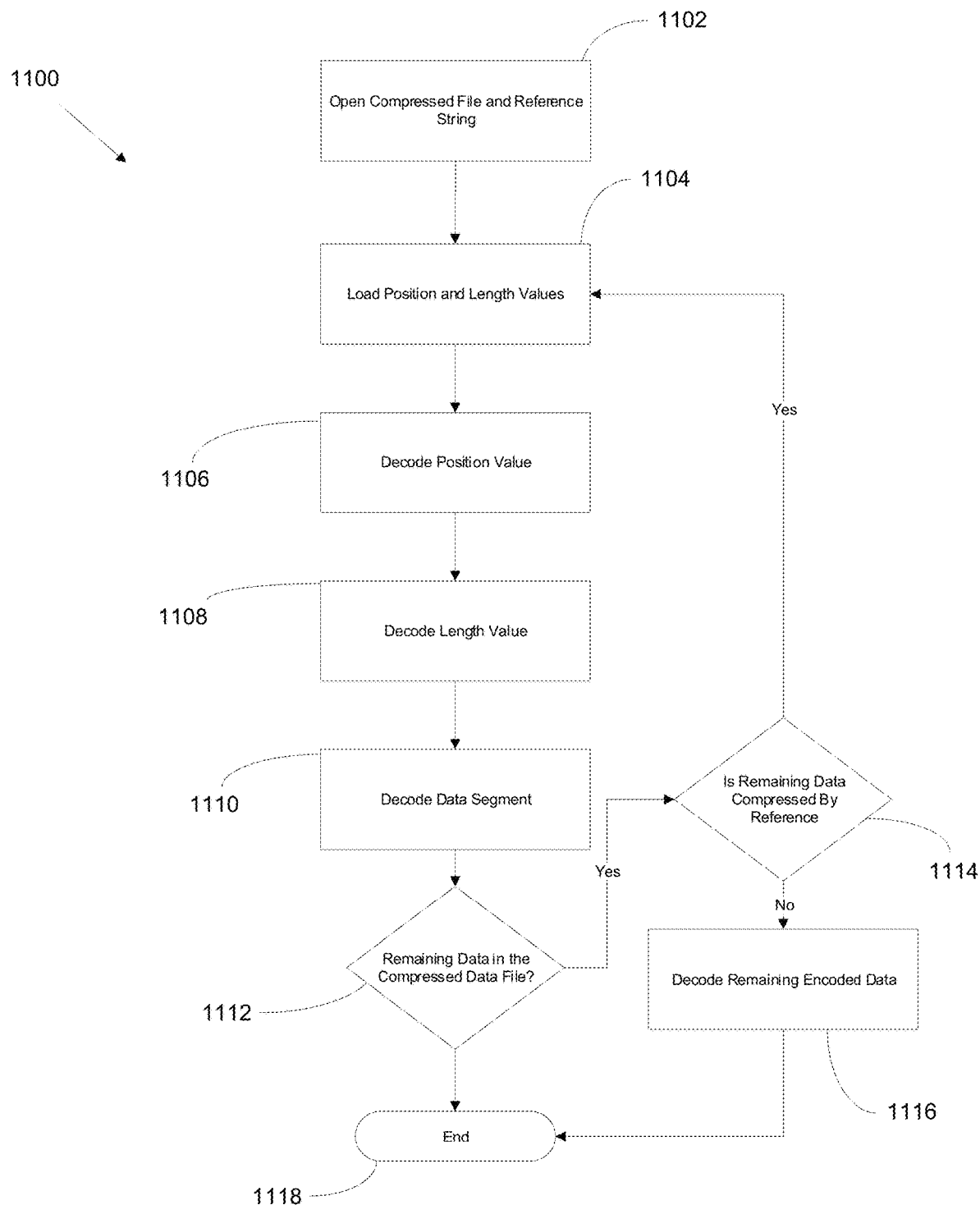
FIG. 12 is a flow chart illustrating a process for decompressing sequencing data that was compressed using compression by reference.

Turning now to FIG. 12 an example of a reference decompression process 1100 can be seen for decompressing sequencing data compressed using a compression by reference process as discussed above. At process block 1102, the reference decompression process 1100 can open both a received compressed file, along with a reference string associated with the compressed data. In one embodiment, the reference string is previously stored in a memory of the receiving device. Alternatively, the reference string can be transmitted in conjunction with the compressed data. Once the compressed data and the reference file have been opened at process block 1102, a first position and a first length code associated with the received data is loaded at process block 1104. At process block 1106 the position value is decoded with reference to the reference string. The position value being decoded, the length value can then be decoded at process block 1108. Once the position value and the length value have both been decoded, the data segment can be decoded based on the string reference and put into memory at process block 1110. The decompression process 1100 can then determine if there is remaining data in the compressed data file at process block 1112. If there is remaining data, the decompression process 1100 can then determine if the remaining data contains data that was compressed by reference at process block 1114. If the remaining data does contain data that was compressed by reference, the decompression process returns to process block 1104. If data remains that was not compressed by reference, but by other means such as fixed encoding, the remaining data can be decoded at process block 1116. Once the remaining decoding process is completed, the process can end at process block 1118. Similarly, if it is determined that there is no remaining data at process block 1112, the decoding process can also end at process block 1118. For example, if the remaining data is encoded using fixed encoding, the data can be decoded using fixed decoding process. Alternatively, the fixed encoded data can be decoded at process block 1116 using a Huffman decompression process such as that shown in FIG. 11. If it is determined that no data remains in the compression file at process block 1114, the decompression process 1000 can end at process block 1118.

Figure 13:
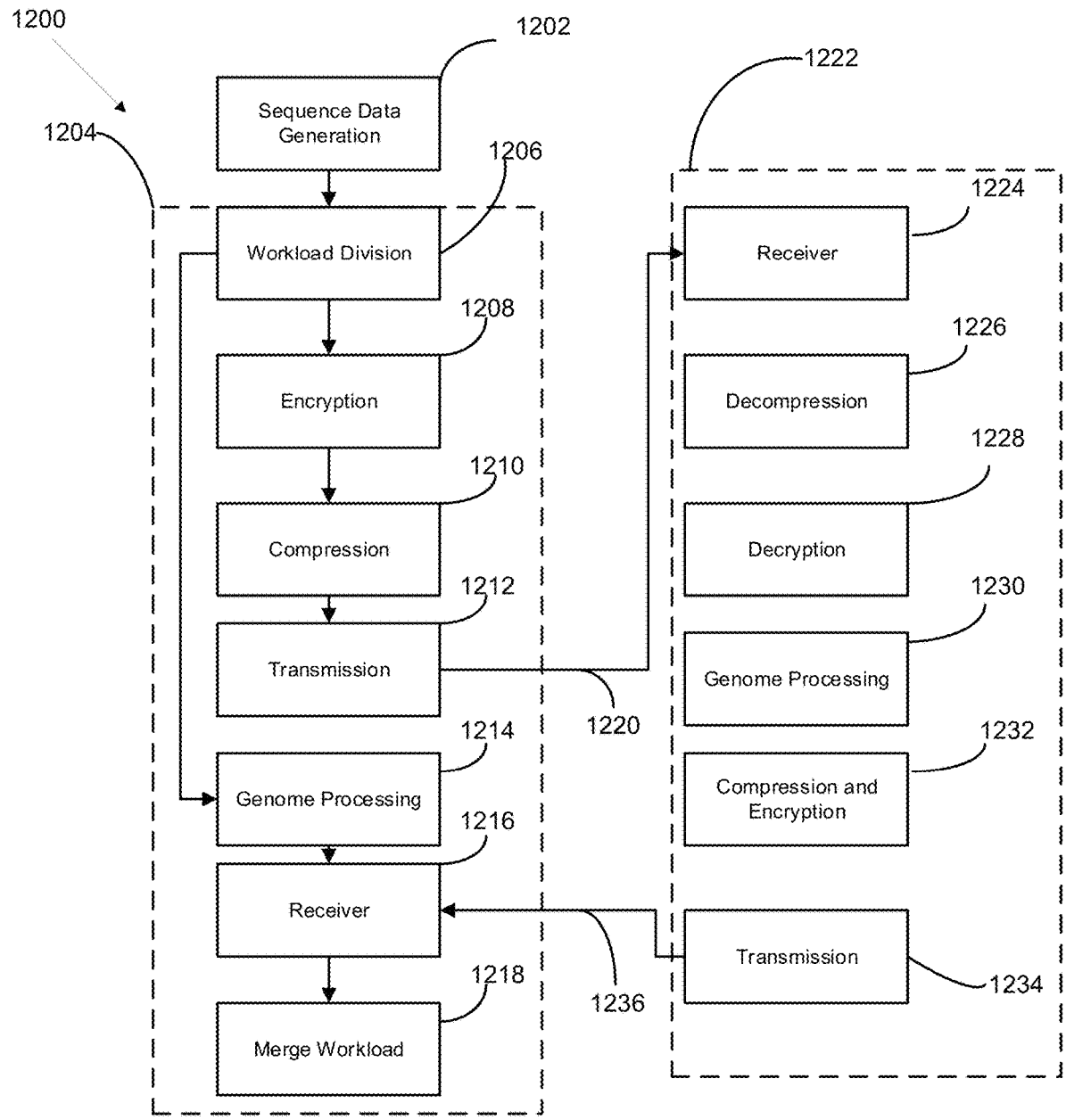
FIG. 13 is a flow chart illustrating a distributive genome communication process.

FIG. 13 shows a flow chart showing a distributive genome communication process 1200. At process block 1202 a biomolecule, e.g. DNA, is sequenced and sequencing data is generated. The sequencing data can then be sent to analysis device 1204. In one embodiment, analysis device 1204 can be a stand alone analysis device. As non-limiting examples the analysis device 1204 could be a dedicated sequence analysis machine, a PC or other computer, or a server. Alternatively, analysis device 1204 could be integral to a sequencing device. The analysis device can contain multiple modules, including a workload division module 1206, an encryption module 1208, a compression module 1210, a transmission module 1212, a genome processing module 1214, a receiver module 1216 and a merge workload module 1218. These modules can be implemented by software, hardware, or a hybrid of software and hardware. Non-limiting examples of hardware implementation could be performed using field-programmable gate arrays (FPGAs), graphical processing units (GPUs) and/or application-specific integrated circuits (ASICs).

The sequencing data can be sent to the workload division module 1206 to determine how to divide the workload between multiple analysis devices. In one embodiment, the workload division module 1206 is aware of all other analysis devices in a distributed network and can use that information to determine how best to divide the workload between the distributed devices. The workload division module 1206 can receive information from external devices that can be used to determine how to divide the workload. This information can include, loading information, computation power, available memory, time availability, and network connectivity speed, as non-limiting examples. Additionally, the workload division module 1206 can have either known or collected statistics relating to the performance of the multiple analysis devices to which it has access. Non-limiting examples of these statistics can include individual thread speed, average processing times, etc. In one example, the workload division module 1206 can collect these values over time which can allow for accurate distribution of work where the performance of a particular analysis device does not perform as specified.

Once the workload division module 1206 determines how the workload is to be divided, the data that is to be processed by the analysis device 1204 can be transmitted to data processing module 1214 for processing. The remaining data can be transmitted to process block for encryption at encryption module 1208. The data can be encrypted using various types of encryption as discussed above. Once the data is encrypted, it is then compressed at compression module 1210. The data can be compressed using the methods described, including read data compression and compression by reference. Once the data is compressed, it can be sent to the transmission module 1218 to be prepared for transmission. The data can be transmitted using applicable transmission protocols, including those discussed above. The data can then be transmitted over communication link 1220. In one embodiment, the communication link 1220 can be a wired link such as an Ethernet cable such as CAT 5. The communication link 1220 could also be other wired connections such as serial, USB, Firewire, or fiber optic. Alternatively, the communication link 1220 can be a wireless link such as Wi-Fi, Bluetooth, satellite communication, cellular communication, etc. The data, having been transmitted over the communication link 1220 can be received by a second analysis device 1222. While two analysis devices are shown in this example, more than two analysis devices can be used, as applicable. The data is received by the reception module 1214 of the second analysis device 1222.

Once the data has been received by the receiver module 1224, the data can then be decompressed at the decompression module 1226. The decompression module 1226 can use decompression methods such as those discussed above, but could use any decompression methodology suitable to decompressed the received compressed data. After the data has been decompressed, it can then be decoded at decryption module 1228. Decryption module 1228 can use decryption methodologies corresponding to the encryption methodologies employed at encryption module 1208. Once the data has been decrypted, it can be sent to processing module 1230 for processing. Once the data has been processed, it can then be compressed and encrypted at compression and encryption module 1232. The compressed and encrypted data can then be sent to transmission module 1234 for preparation to be transmitted. The data can be then be transmitted via communication link 1236 to the reception module 1216 on the first analysis device 1204. While communication link 1236 is shown separately from communication link 1220 it should be understood that communication links 1220 and 1236 can be the same communication link. Additionally, while the example in FIG. 12 shows the data from the second analysis device 1222 being transmitted to first analysis device 1204, the data could alternately be sent to one or more other analysis devices, as well as other devices for further processing.

The data being received by reception module 1216 of the first analysis machine 1204 can then be merged with other work performed by the first analysis machine 1204 at data merging module 1218. In one embodiment, data merging module 1218 can combine the processed data into a complete data set for further analysis.

Compression of the sequencing data allows for more compact transmission and communication of the sequencing data. However, as discussed above, the data contained within the sequencing data can contain private or confidential information. Accordingly, methods of encrypting the data to be compressed and transmitted can be used to protect the content of the data. In one example, a single cipher type encryption process can be used. Single cipher encryption has the advantage of being nearly impossible to decode by another, if done correctly. In general, a random key is generated that has a corresponding value for each value (character, bit, etc.) in the data to be encrypted. To be done correctly, the key must be truly random, it can only be used once, and it must be kept completely secret.

Figure 14:
FIG. 14 is an illustrative example of modulo addition (SEQ ID NOs:43-45).

Single cipher encryption, can be done using several implementation. One of the implementation is through the use of a "one time pad." One time pad encryption relies on a one time use cipher key to encode and decode a data set. This encryption can be applied to biomolecular data, such as genome sequencing. In one embodiment, one time pad encryption can utilize modulo addition of a data set and a key to form a cipher. FIG. 14 illustrates an example of modulo addition 1400 using base data (A, C, G, T). For the read data set 1402, each base can be associated with an integer. The read data 1402 can be direct read data, or compressed read data. For example: A=0; C=1; G=2; and T=3. Thus, when G(2) is added to T(3), a C(1) is obtained; or when A(0) is added to G(2), a G(2) is obtained. Additionally, if the compression of the data has converted the data from ASCII based letters to base 2 values, similar assignment of values to the base-2, or other values, can be performed. While modulo 4 is used for four base values (A, C, G, T), modulo 5 can be used in cases where N's can be used as well in the read data. Additionally, where other biological data is available (proteins, methylated phenotype, etc), similar modulo addition types can be used.

In operation, once the read data set 1402 has been determined, a key 1404 can be generated. This key can be a random generation of base values. Alternatively, the key could be based on a circular reference genome. A circular reference genome can be a string of genomic data that can be repeated over and over again to create a length sufficient to serve as a cipher key 1404. In one embodiment, a reference human genome can be used as the circular reference genome. Additionally, genomes of animals, plants, or other organisms can be used as the circular reference genome. Once a genome is selected, a nucleotide base (A, C, G, T), of which the human genome contains some six billion, is randomly chosen as the starting point within the genome. This starting point can be the position from which the modulo addition with the read data begins. Multiple genomes may be used as circular reference genomes to increase the random nature of the key. These circular reference genomes must exist on both the encryption and decryption side to ensure proper decryption of the reads is possible.

Once the key has been generated, the read data 1402 can be modulo added to the key 1404 to produce a cipher 1406. This cipher 1406 can be essentially random data once it is generated due to the random selection of the key 1404.

Figure 15:
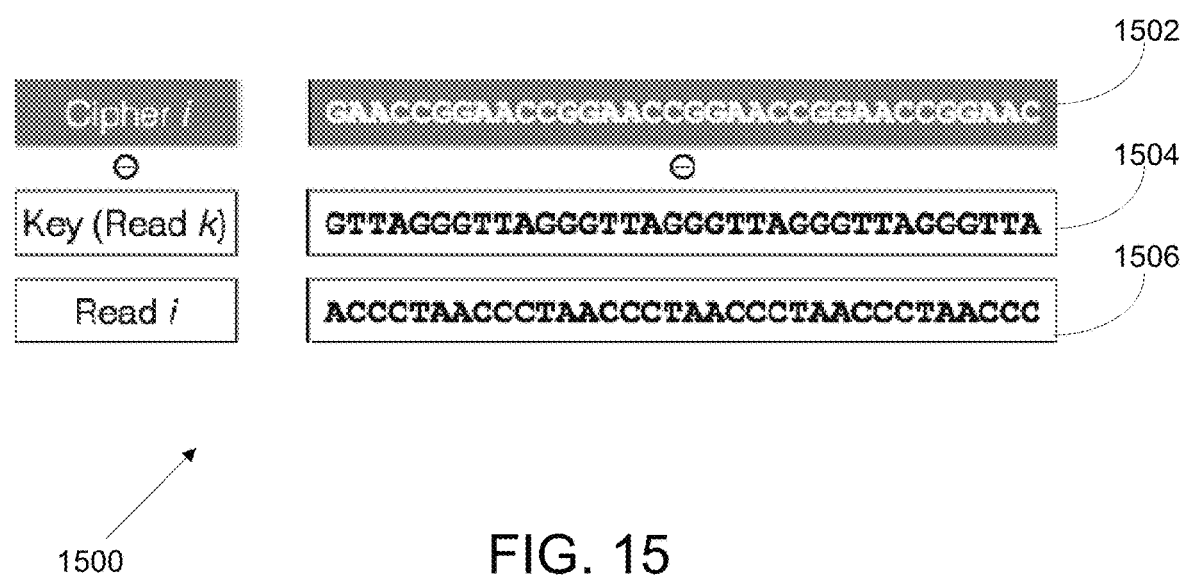
FIG. 15 is an illustrative example of modulo subtraction (SEQ ID NOs:46-48).

Turning now to FIG. 15, a decryption of a single use cipher 1500 can be seen. A single use cipher 1502 having been received, can be decoded using modulo subtraction. In order for the single use cipher 1502 to be properly decoded, the numerical values associated with each base element (A, C, G, T) must be the same as that used when the single use cipher 1502 was created using modulo addition. The single use cipher 1502, having been received, can be modulo subtracted using a read key 1504. To ensure proper decryption, the read key 1504 must be the same as the key used to encode the original data. The read key 1504 can be modulo subtracted from the single use cipher 1502 to obtain the decrypted read data 1506.

Figure 16:
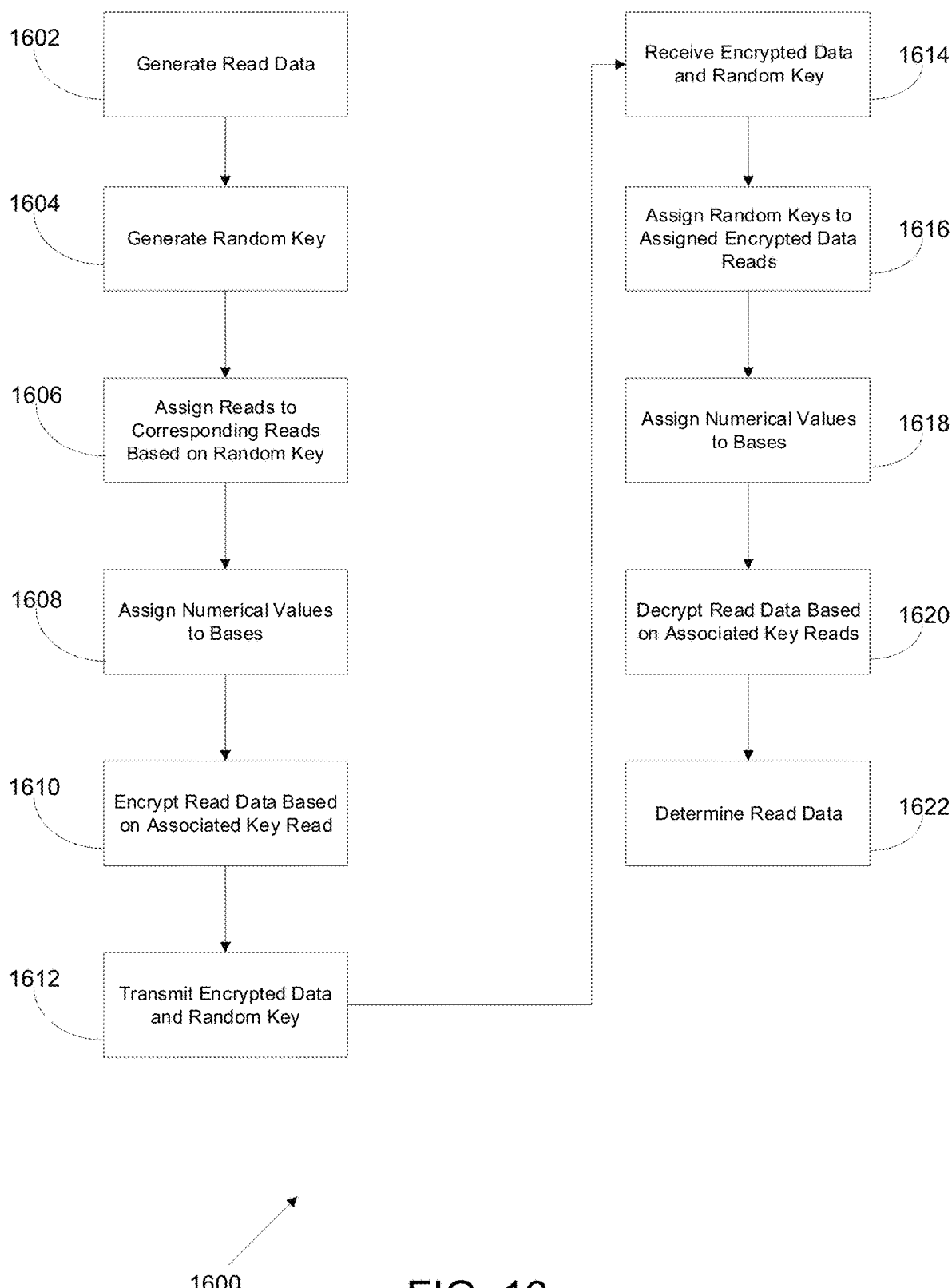
FIG. 16 is a flow chart illustrating a single cipher encryption process.

FIG. 16, a single cipher encryption process 1600 based on read data can be seen. Single cipher encryption process 1600 can use obtained read data as the encryption key, instead of using random keys such as the circular genome references discussed above. At process block 1602 a set of read data can be generated. In one embodiment, the read data can be in the form of a FASTQ file. FASTQ files can be raw sequencing files containing varying numbers of reads. For example, a 30× coverage FASTQ raw sequencing file can include close to 900,000,000 reads. Single cipher encryption process 1600 can use the reads data to generate keys when compressing the read data itself.

At process block 1604 a random key can be generated. In one embodiment, a first read from the set of read data can serve as the key for a second read from the set of read data. The generation of the random key can determine which reads are to be paired with each other to create encryption keys. This can continue for all of the reads in the set of read data. In one embodiment, the assignment of one read to another read for purposes of generating an encryption key, can be done using a randomization algorithm. Additionally, more than one randomization algorithm can be used to increase the randomness for the pairings of read data. Once the random keys have been generated, the reads can be associated with each other at process block 1606.

Once the reads have been randomly assigned to other reads, numerical values can be assigned to the bases (A, C, G, T) contained within the individual reads at process block 1608. Numerical values can be assigned to the bases contained within both the data read, and the paired key read. Once the numerical values have been assigned to the individual bases contained within both the data read and the associated key read, the data read and the assigned key read are added using modulo addition at process block 1610. In one embodiment, the modulo addition can be modulo 4 additional. However, other types of modulo addition can be used based on the data set to be encrypted.

Figure 17:
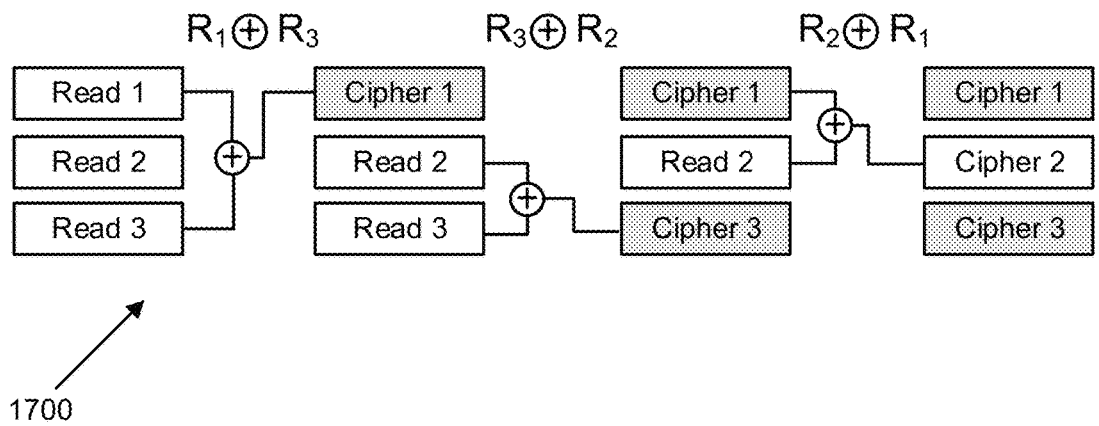
FIG. 17 is an example of a biological data read encryption process using modulo addition.

Turning briefly to FIG. 17, an example read encryption process 1700 can be seen. The example process 1700 assumes a limited set of three reads from a set of read data designated as R1, R2 and R3, the reads can be assigned to each other based on the randomly generated key. In this example, R1 can be assigned to R3; R3 can be assigned to R2, and R2 can be assigned to R1. This can result in R3 being the key of R1 to obtain cipher C1; R2 can be the key for R3 to obtain cipher C3 and R1 can be the key for R2 to obtain cipher C2. In some examples, the original, unencrypted read data can be used in all of the modulo addition processes to generated the ciphers. However, in one embodiment, the encrypted read data can be stored to a memory and then used in lieu of the original read data in encrypting an assigned read data. For example, in FIG. 17 it can be seen that R1 can be first modulo added to R3 to create cipher C1. Cipher C1 can then be stored into memory, replacing R1. Thus, when R2 is encrypted, it can be modulo added to C1, in lieu of R1. Generality of the cipher can be maintained, even when used as a key, as the cipher can be composed of the same elements as the data reads due to the nature of the modulo operations.

Returning to FIG. 16. the data reads having been encrypted, the encrypted data can be transmitted to a receiving unit at process block 1612, such as an analysis machine, along with the random key. The random key can be transmitted along with the encrypted data in the same transmission. Alternatively, the random key can be transmitted to the receiving unit separately to maintain security. For example, while the encrypted read data can be transmitted over an internet protocol such as TCP/IP, UDP, etc., the random key can be transmitted over a secure connection such as VPN. Alternatively, the random key can be stored on a removable storage device such as a flash memory device, a CD-ROM, DVD, SSHD, etc.

The encrypted read data and the random key can be received by the receiving unit at process block 1614. Once the data and the random key have been received, the random key can be used to assigned the appropriate data reads to each other in process block 1616. This assignment can be the same as was used in the encryption process at process block 1606. The encrypted reads being having been assigned to each other at process block 1616, numbers can be assigned to each of the bases (A, C, G, T) at process block 1618 Subsequently, at process block 1620 the read data can be modulo subtracted from the paired key reads. While the type of modulo subtraction (modulo 4, modulo 5, etc.) can vary, the modulo type used for subtraction at process block 1620 should be the same as the modulo type used at process block 1610. The modulo subtraction completed, the read data can be determined at process block 1622.

The above single cipher encryption process 1600 based on read data can allow one time pad type encryption to be applied to raw sequencing data. Further, by using the data reads as the encryption keys, the need for having a separate, random key for every read is eliminated.

Figure 18:
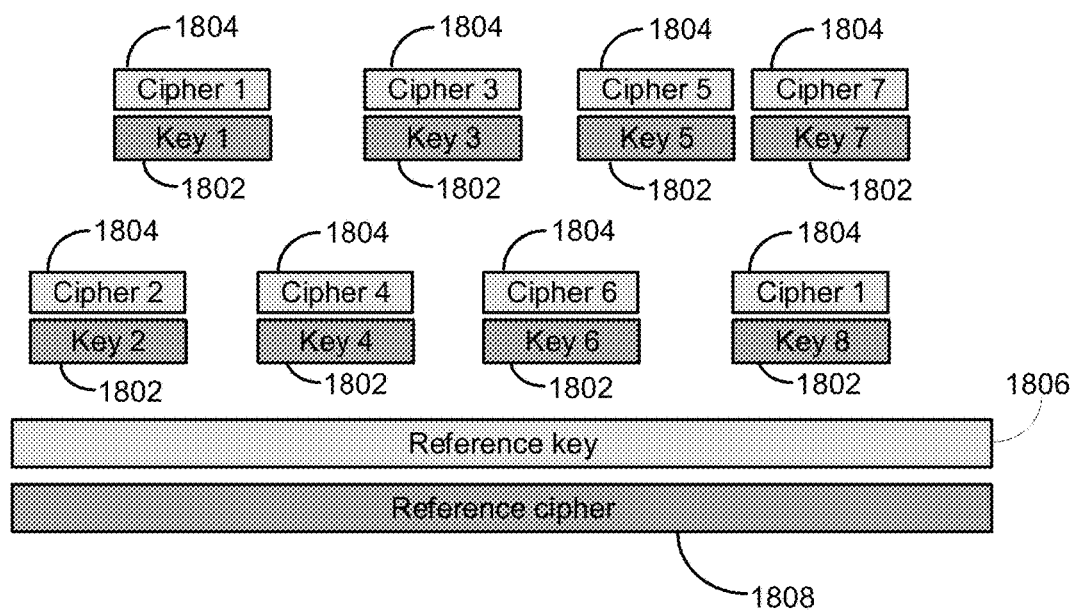
FIG. 18 is a pictorial representation of compression by reference of multiple reads.

Additionally, using read data based single cipher encryption as described above can allow for the encrypted data to be utilized by the above mentioned compression processes without being decrypted. Specifically, as the key to the cipher can be present in the read data scenario, it can be possible to encrypt the read data prior to performing any further operations. For example, FIG. 18 shows a pictorial representation of compression by reference of multiple reads 1800. In this example the read data can be encrypted using the associated keys 1802 to create cipher reads 1804. Further a reference string can be encrypted using a reference key 1806 to create an encrypted reference cipher 1808. The compression by reference process can then proceed by aligning the ciphered reads 1804 and keys 1802 with the encrypted reference cipher 1808 and assigned reference key 1806. In one embodiment, the compression by reference process can be the compression by reference process described in FIG. 10 and the specification above. While the example of FIG. 18 illustrates a compression by reference operation, read data based single cipher encryption can also be used for other genomic-type and non-genomic-type operations, such as alignment, while using encrypted data.

The present invention has been described in terms of one or more preferred embodiments, and it should be appreciated that many equivalents, alternatives, variations, and modifications, aside from those expressly stated, are possible and within the scope of the invention.

The invention claimed is:

1. A device for encrypting subject data, the device comprising:
 a communication link, the communication link capable of receiving a set of subject data, the set of subject data including a plurality of subject data reads, the plurality of subject data reads having at least one data point;
 an encryption module, the encryption module configured to encrypt the plurality of subject data reads using a single cipher encryption method, wherein the encryption module executes an encryption process, the encryption process comprising the steps of:
  generating a plurality of random keys based on the received plurality of subject data reads, each of the plurality of random keys includes a plurality of key data points;
  assigning a random key of the plurality of random keys to an assigned subject data read of the plurality of subject data reads, wherein the plurality of key data points is equal to a number of data points in the assigned subject data read;
  assigning one of the plurality of subject data reads to be a key of a subsequent subject data read, wherein the one of the plurality of subject data reads includes a second plurality of data points equal to a number of data points in the subsequent subject data read;
  assigning numerical values to the plurality of key data points and the second plurality of datapoints, each of the numerical values based on the value of the respective data point;
  executing a modulo adding process to add the numerical values of the random key to the numerical values of the assigned subject data read; and
  generating an encrypted subject data read; and
 a transmission module, the transmission module configured to transmit the encrypted subject data read.

2. The device of claim 1, wherein the set of subject data is DNA sequence data.

3. The device of claim 1, wherein the at least one data point is a DNA base nucleotide.

4. A method of encrypting subject data, the method comprising:
 generating, for each of a plurality of subject data reads, a random key using a circular reference genome;
 associating each of the plurality of random keys to a subject data read of the plurality of subject data reads, such that each subject data read is associated with a different random key;
 assigning numerical values to data points included in the plurality of subject data reads, the numerical value based on the value of the respective data point; and
 performing a modulo adding process to add numerical values of the random key to the numerical values of the associated subject data read to generate an encrypted subject data read.

5. The method of claim 4, wherein the encrypted subject data read can be decrypted using a modulo subtraction process to subtract the values of the random key from the encrypted subject data read.

6. A method of encrypting subject data, the method comprising:
 generating, for each of a plurality of subject data reads, a random key of a plurality of random keys based on the plurality of subject data reads, including assigning one of the plurality of subject data reads to be a key of another subject data read;
 associating each of the plurality of random keys to a subject data read of the plurality of subject data reads, such that each subject data read is associated with a different random key;
 assigning numerical values to data points included in the plurality of subject data reads, each numerical value based on the value of the respective data point; and
 performing a modulo adding process to add numerical values of a random key to the numerical values of the associated subject data read to generate an encrypted subject data read.

7. The method of claim 6, wherein the encrypted subject data read can be decrypted using a modulo subtraction process to subtract the values of the random key from the encrypted subject data read.

* * * * *